United States Patent
Al-Qahtani

(10) Patent No.: US 9,119,974 B2
(45) Date of Patent: *Sep. 1, 2015

(54) SKIN CREAM

(71) Applicant: Ahmed H. Al-Qahtani, Irvine, CA (US)

(72) Inventor: Ahmed H. Al-Qahtani, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/945,120

(22) Filed: Jul. 18, 2013

(65) Prior Publication Data

US 2015/0023908 A1      Jan. 22, 2015

Related U.S. Application Data

(63) Continuation-in-part of application No. 13/041,197, filed on Mar. 4, 2011, now Pat. No. 8,518,879.

(51) Int. Cl.
| | | |
|---|---|---|
| A61Q 19/00 | (2006.01) | |
| A61K 8/64 | (2006.01) | |
| A61Q 19/08 | (2006.01) | |
| A61K 38/20 | (2006.01) | |
| A61K 38/08 | (2006.01) | |
| A61K 38/18 | (2006.01) | |
| A61Q 7/00 | (2006.01) | |
| A61K 8/81 | (2006.01) | |
| A61K 8/98 | (2006.01) | |
| A61K 8/02 | (2006.01) | |
| A61Q 5/00 | (2006.01) | |
| A61K 8/97 | (2006.01) | |

(52) U.S. Cl.
CPC .............. *A61Q 19/08* (2013.01); *A61K 8/0254* (2013.01); *A61K 8/64* (2013.01); *A61K 8/8117* (2013.01); *A61K 8/97* (2013.01); *A61K 8/98* (2013.01); *A61K 8/985* (2013.01); *A61K 38/08* (2013.01); *A61K 38/1841* (2013.01); *A61K 38/202* (2013.01); *A61K 38/204* (2013.01); *A61K 38/2046* (2013.01); *A61K 38/2053* (2013.01); *A61Q 5/00* (2013.01); *A61Q 7/00* (2013.01); *A61Q 19/00* (2013.01); *A61K 2800/412* (2013.01); *A61K 2800/56* (2013.01)

(58) Field of Classification Search
CPC ........... A61K 8/14; A61K 8/64; A61K 8/922; A61K 8/97; A61K 2300/00; A61K 2800/412; A61K 8/985; A61K 9/0014; A61Q 19/00; A61Q 19/08

See application file for complete search history.

(56) References Cited

U.S. PATENT DOCUMENTS

| | | | |
|---|---|---|---|
| 8,138,147 B2 * | 3/2012 | Naughton et al. | 514/8.1 |
| 8,410,055 B2 | 4/2013 | Li et al. | |
| 2009/0117061 A1 * | 5/2009 | Gross | 424/59 |
| 2010/0035815 A1 | 2/2010 | Li et al. | |
| 2011/0014251 A1 | 1/2011 | Ray | |
| 2011/0301090 A1 | 12/2011 | Li et al. | |
| 2012/0107413 A1 | 5/2012 | Lim et al. | |
| 2013/0052647 A1 * | 2/2013 | Goldrick et al. | 435/6.12 |
| 2013/0143314 A1 * | 6/2013 | Shiels et al. | 435/320.1 |
| 2013/0209528 A1 * | 8/2013 | Levi et al. | 424/400 |

OTHER PUBLICATIONS

Taylor, Douglas; et al., Exosome Isolation for Proteomic Analysis and RNA Profiling, Serum/Plasma Proteomics: Methods and Protocols, May 2011, pp. 235-246, vol. 726, Humana Press, New York, USA.

Meredino, Anna; et al., Hsp60 Is Actively Secreted by Human Tumor Cells, PLoS One, Feb. 2010, vol. 5, Issue 2.

Mittelbrunn, Maria; et al., Intercellular Communication: Diverse Structures for Exchange of Genetic Information, Nature Review: Molecular Cell Biology, May 2012, p. 328-335, vol. 13, Issue 5, Nature Publishing Group, New York, USA.

* cited by examiner

*Primary Examiner* — Daniel C Gamett

(57) ABSTRACT

The present invention relates to skin care compositions, including cosmeceuticals, for topical application, and more particularly, a skin cream, comprising exosomes and cell culture medium conditioned by cells grown in two-dimensional culture. Also included are methods of making and using such compositions and kits comprising the skin cream therein.

17 Claims, 18 Drawing Sheets

Before and After

After 5 treatments

Before and After

Acne Scars

Growth factors and hair

Week 0  Week 8  Week 15

Growth factors and hair

Week 0

Week 15

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Pro Collagen Fragment

<400> SEQUENCE: 1

Lys Thr Thr Lys Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Palmitoyl Substituted
<220> FEATURE:
<221> NAME/KEY: LIPID
<222> LOCATION: (1)..(1)
<223> OTHER INFORMATION: PALMITATE

<400> SEQUENCE: 2

Lys Thr Thr Lys Ser
1               5
```

SKIN CREAM

CROSS REFERENCE TO RELATED APPLICATION

This application is a continuation-in-part of U.S. application Ser. No. 13/041,197, filed Mar. 4, 2011, now U.S. Pat. No. 8,518,879.

BACKGROUND OF THE INVENTION

1 Field of the Invention

The present invention is generally related to skin care compositions, and more specifically to cosmeceuticals and medicaments for topical application, including a skin cream, comprising exosome enriched cell culture medium conditioned by foreskin-derived fibroblast cells grown in two-dimensional culture.

2 Background Information

Currently there is no cure for aging skin and treatments for aging and/or wrinkled skin are temporary and suffer from drawbacks and side effects. The loss of collagen and elastic proteins present in the dermal layers causes a breakdown of resiliency and skin thickness over time, which may result in fine lines and wrinkles. The most common surgical interventions available for treatment of facial wrinkles include facelifts, laser surgery, skin peels, and injection therapies, such as BOTOX®. However, surgical methods may result in detrimental complications, are often painful, and must be repeated with time. Non-invasive remedies include topical formulations consisting of alpha/beta hydroxy, retinoic acids, argirelines, and vitamins. However, none of these methods completely eliminate wrinkles, and require multiple, and often expensive treatments. Some topical formulations may act as irritants to the skin, to elicit wound healing responses, but do not successfully replenish the thinning skin with adequate proteins for treatment and/or prevention of age-related defects.

The pathogenesis of skin aging is well defined; it is characterized by a decrease in collagen synthesis and an increase in collagen breakdown, mediated by metalloproteinases (Arch. Dermatol. 138[11]:1462-70, 2002). This net loss in dermal collagen is believed to contribute to and/or permit wrinkling. Biologic factors that stimulate collagen production in wound healing might provide benefits for aging skin. Accordingly, growth factors, peptide fragments, and other biologically active molecules are being incorporated into anti-aging cosmeceuticals.

Growth factors are typically peptides with diverse biological effects. Some growth factor families that have been identified as useful in wound healing and/or epidermal remodeling include, e.g., transforming growth factor-β (TGF-β), epidermal growth factor (EGF), insulin-like growth factors (IGFs), platelet-derived growth factor (PDGF), and fibroblast growth factors (FGFs).

Living cells cultured in vitro secrete extracellular proteins and peptides, including growth factors, into the nutrient medium in which they are cultured. Medium exposed to cells in culture is referred to as "conditioned medium." Naughton et al., in U.S. Pat. No. 6,372,494, teach that conditioned medium from cell cultures comprising a three-dimensional extracellular matrix and multiple layers of stromal and tissue specific cells (i.e., a three-dimensional culture system) may be used advantageously to prepare growth factor-enriched cosmeceutical compositions; U.S. Pat. No. 6,372,494 is herein incorporated in its entirety by reference thereto. Indeed, Naughton et al. assert that the complex three-dimensional culture systems have numerous advantages over simple two-dimensional culture systems, e.g., greater surface area; more analogous to tissues in vivo; absence of "contact inhibition" (a limitation on the growth of cells in two-dimensional cultures); creation of localized microenvironments; increased cell-cell interactions and potential cell migration; maintenance of a differentiated phenotype and elaboration of differentiation factors, etc. Unfortunately, three-dimensional culture systems are substantially more expensive and technically challenging to establish and maintain than conventional two-dimensional culture systems. Moreover, the complex biological systems formed in three-dimensional culture create so many variables (e.g., cell-cell and cell-matrix interactions, tissue differentiation, etc.), that quality control with respect to the harvested conditioned medium becomes nearly impossible, and batch-to-batch variability in growth factor composition may be commercially unacceptable.

In addition, cultured cells also produce extracellular vesicles. Extracellular vesicles, or exosomes, have emerged as potent vehicles for cell-to-cell communication since the discovery that they contain functional mRNA, miRNA, DNA, and protein molecules that can be taken up by target cells. The genetic information contained in exosomes can influence or even direct the fate of the target cell, for example by triggering target cell activation, migration, growth, differentiation or de-differentiation, or by promoting apoptosis or necrosis. As such, exosomes can provide additional cell factors which assist in wound healing and/or epithelial remodeling.

Accordingly, while the use of growth factors to treat aging skin is gaining favor among skin care professionals, there remains an important and unmet need for more effective topical formulations for the treatment and/or prevention of skin damage, wrinkles and/or other defects due to aging and environmental factors, where the formulations comprise conditioned medium enriched with vesicles, growth factors, and/or extracellular matrix compositions produced by economical, well-controlled cell culture methods.

SUMMARY OF THE INVENTION

The present invention relates to skin care compositions, including cosmeceutical, for topical application, and a skin cream, comprising cell culture medium conditioned by cells, which medium may be exosome enriched. The present invention also discloses methods of using such compositions for the treatment of skin disorders.

In embodiments, a skin cream for treating a skin defect is disclosed, including exosome enriched conditioned medium from cultured substantially homogenous foreskin derived fibroblast cells, where the exosomes are isolated from cultures of cells under conditions adapted to promote secretion of at least one growth factor into nutrient medium.

In one aspect, the exosomes are isolated from conditioned medium that is the same as or is different from the exosome enriched conditioned medium. In a related aspect, the conditioned media are different. In a further related aspect, the exosome enriched conditioned medium is generated from transformed cells and the exosomes are isolated from conditioned medium generated from non-transformed cells or the exosome enriched conditioned medium is generated from non-transformed cells and the exosomes are isolated from conditioned medium generated from transformed cells.

In another related aspect, the transformed cells are from a cell line designated as ATCC Accession No. PTA-11680 and the non-transformed cells are from a cell line designated as ATCC Accession No. PTA-11681.

In one aspect, the skin cream further includes one or more solvents, a base solvent, one or more botanicals, and one or more emollients.

In another aspect, the exosomes include at least one molecule selected from a protein, DNA, RNA, and combinations thereof.

In one aspect, the skin cream includes TGF Beta-1, TGF Beta-2, TGF Beta-3, IL-3, IL-6, IL-7, and IL-8, and the conditioned media is present at a concentration of at least about 5-20% (wt %).

In another aspect, the skin cream includes about 1-3 ng/mL TGF Beta-1, about 100-160 pg/mL TGF Beta-2, about 50-100 pg/mL TGF Beta-3, about 60 pg/mL IL-3, about 11 pg/mL IL6, about 50 pg/ML IL-7, and about 4-10 pg/mL IL-8, and the conditioned media is present at about 30-42% (wt %).

In one aspect, the skin cream includes an additional agent. In a related aspect, the additional agent includes Pal-KTTKS (SEQ ID NO:2) or argireline.

In one embodiment, a method of cosmetically or pharmaceutically treating at least one condition of the skin or hair of a subject is disclosed including administering to a subject in need thereof a composition comprising a conditioned medium or extract or concentrate thereof, from cultured substantially homogenous transformed foreskin derived fibroblast cells, where the cells are transformed with SV40 Large T Antigen, and where the conditioned medium is generated by incubating a nutrient medium with said cells in two-dimensional culture under conditions adapted to promote secretion of at least one growth factor into the nutrient medium, and one or more ingredients selected from glycerin, panthenol, biotinyoyl tripeptide-1, *Lonicera Caprifolium* flower extract, *Lonicera Japonica* flower extract, 1,2-hexanediol, caprylyl glycol, *Simmondsia Chinensis* seed oil, xanthan gum, hydroxyethyl acrylate/sodium acryloyldimethyl taurate copolymer, squalane, polysorbate 60, *Rosmarinus Officinalis* leaf oil, lactic acid, and chlorphenesin, where the at least one growth factor is present in the conditioned medium or extract or concentrate thereof in an amount sufficient to treat the skin defect.

In one aspect, the condition of the skin or hair is treated cosmetically by at least one of: a) inducing increased skin integrity by cell renewal; b) enhancing water content or moisture of skin; c) reducing trans epidermal water loss, skin flaking and scaling; d) improving skin thickness; e) enhancing skin tensile properties f) reducing the appearance of dermal wrinkles and improving skin texture; d) reducing skin pores size and enhancing skin smoothness; o) rejuvenating or renewing vulvo-vaginal structures; p) improving the appearance of scars and skin abrasions; q) decreasing oily skin by minimizing sebaceous gland secretion; r) reducing chronological, intrinsic and extrinsic dermal aging of the skin; s) improving skin age spots; t) enhancing hair pigmentation; and u) improving skin tone.

In a related aspect, the condition of the skin is treated cosmetically by rejuvenating vulvo-vaginal structures in a subject. In a further related aspect, the composition comprises glycerin at about 20.00% (w/w), *Simmondsia Chinensis* seed oil at about 18.00% (w/w), xantham gum at about 1.00% (w/w), hydroxyethyl acrylate/sodium acryloyldimethyl taurate copolymer at about 0.66% (w/w), squalane at about 0.17% (w/w), polysorbate 60 at about 0.17% (w/w), *Rosemarinus Officinalis* leaf oil at about 0.80% (w/w), lactic acid at about 0.15% (w/w), and chlorphenesin at about 0.30 (w/w).

In another aspect, the condition of the skin or hair is treated pharmaceutically by at least one of: a) increasing blood flow in the skin; b) improving skin temperature and thermoregulation of the skin; c) increasing dermal thickness and inhibiting fibroblast cell apoptosis; d) inducing collagen production and increasing skin turgor; e) inducing elastin production and increasing skin elasticity; f) inhibiting elastase to improve skin texture and dermal lines; g) repairing and treating wrinkles and improving skin texture; h) positively influencing vascularization, skin thickness and skin turgor, and slowing down the process of aging; i) decreasing matrix metalloproteinases to positively influence skin collagen and elastin; j) enhancing skin repair and wound healing; k) improving appearance of scars and skin abrasions; l) decreasing oily skin by improving sebaceous gland function; m) stabilizing skin color changes and hair pigmentation and enhancing skin lightening; n) treating, ameliorating and protecting against hyperpigmentation, age-spots and photo-aging; o) decreasing or eliminating acne; p) decreasing scalp hair loss or enhancing the retention of scalp hair (in male and female pattern baldness); q) decreasing facial hair loss; r) reducing apocrine gland secretions and reducing excessive sweat gland function (hindradentitis and osmidrosis); s) reducing inflammation of skin and vaginal dryness; and t) attenuating skin and hair abnormalities in steroid hormone synthesis and function and metabolism of steroids and binding steroid receptors involving androgenic and/or estrogenic effects.

In a related aspect, the condition of the skin is treated pharmaceutically by decreasing facial hair loss in a subject, where the facial hair is eyelash hair. In a further related aspect, the composition comprises glycerin at about 1.47% (w/w), panthenol at about 0.500% (w/w), biotinoyl tripeptide-1 at about 0.003% (w/w), *Lonicera Caprifolium* flower extract at about 0.100% (w/w), *Lonicera Japonica* flower extract at about 0.100% (w/w), 1,2-hexanediol at about 0.400% (w/w), and caprylyl glycol at about 0.400% (w/w).

In one embodiment, a kit is disclosed including a) a skin cream as described above; b) a container; c) a label; d) an optional applicator; and e) instructions which provide methods of applying the skin cream. In a related aspect, the kit further includes one or more ingredients selected from Pal-KTTKS (SEQ ID NO:2), argireline, glycerin, panthenol, biotinoyl tripeptide-1, *Lonicera Caprifolium* flower extract, *Lonicera Japonica* flower extract, 1,2-hexanediol, caprylyl glycol, *Simmondsia Chinensis* seed oil, xantham gum, hydroxyethyl acrylate/sodium acryloyldimethyl taurate copolymer, squalane, polysorbate 60, *Rosemarinus Officinalis* leaf oil, lactic acid, and chlorphenesin.

In embodiments, a composition is disclosed for the treatment of atrophic vaginitis or vaginal dryness. In other embodiments, a composition is disclosed for the treatment of milphosis or madarosis.

In one embodiment, a method of making a skin cream is disclosed including culturing a first substantially homogenous set of cells; harvesting the medium conditioned by the first set of cells; optionally, culturing a second substantially homogenous set of cells; harvesting the medium conditioned by the second set of cells; isolating exosomes from the conditioned medium of the first or second set of cells; adding the isolated exosomes to the conditioned medium from the first or second set of cells to form a conditioned medium containing an enriched population of exosomes; and adding the conditioned medium containing the enriched population of exosomes to a formulation comprising one or more solvents, a base solvent, one or more botanicals, and one or more emollients to form a cream.

In one aspect, the exosomes are isolated by a method selected from the group consisting of centrifugation, immunoaffinity, chromatography, and combinations thereof.

In another aspect, the set of cells comprises transformed cells from a cell line designated as ATCC Accession No. PTA-11680.

In embodiments, a composition is disclosed comprising a conditioned medium or extract or concentrate thereof, from cultured substantially homogenous transformed foreskin derived fibroblast cells, where the cells are transformed with SV40 Large T Antigen, and where the conditioned medium is generated by incubating a nutrient medium with the cells in two-dimensional culture under conditions adapted to promote secretion of at least one growth factor into the nutrient medium, and glycerin, *Simmondsia Chinensis* seed oil, xantham gum, hydroxyethyl acrylate/sodium acryloyldimethyl taurate copolymer, squalane, polysorbate 60, *Rosemarinus Officinalis* leaf oil, lactic acid, and chlorphenesin, or glycerin, panthenol, biotinoyl tripeptide-1, *Lonicera Caprifolium* flower extract, *Lonicera Japonica* flower extract, 1,2-hexanediol, and caprylyl glycol.

In a related aspect, the transformed cells are from a cell line designated as ATCC Accession No. PTA-11680.

DETAILED DESCRIPTION OF THE INVENTION

Figure 1:
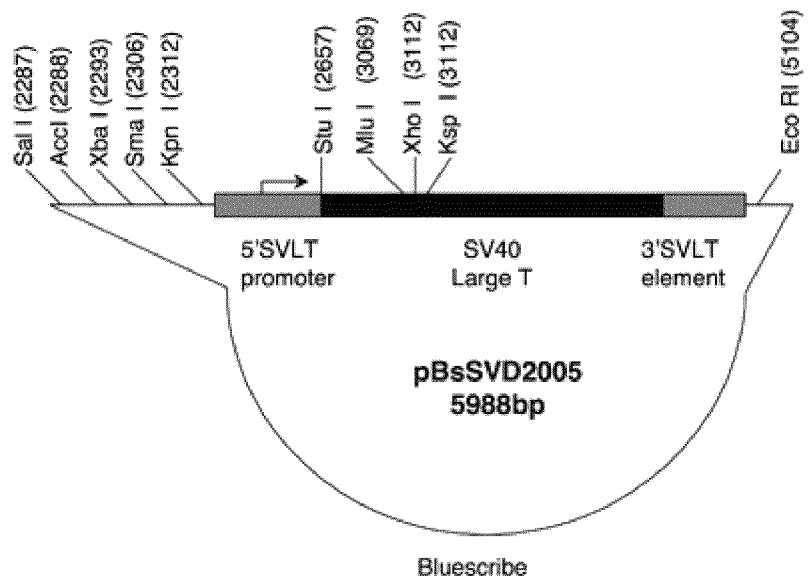
FIG. 1 shows an illustration of an SV40 Large T Antigen containing plasmid: pBsSVD2005.

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a cell" includes one or more cells, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein "exosomes" are defined as cell-derived vesicles that are present in many and perhaps all biological fluids, including blood, urine, and cultured medium of cell cultures, possessing a diameter of between about 30 to about 100 nm, which diameter is larger than LDL, but much smaller than, for example, red blood cells. Exosomes may be released from the cell when multivesicular bodies fuse with the plasma membrane or they may be released directly from the plasma membrane.

As used herein "cosmetically" means a process involving a treatment intended to restore or improve the body's appearance.

As used herein "rejuvenating" or "renewing" means a process (treatment) to restore to an original or a substantially original state from a preprocess (pretreatment) state. For example, a process (e.g., application of skin cream as disclosed) that improves elasticity, tightens and firms the vaginal walls would be included in rejuvenating or renewing said walls after operation of the process.

As used herein "enrich", including grammatical variations thereof, means a process to increase the proportion of a desirable ingredient in a final product over that observed for the un-processed initial product.

Vulvo-vaginal structures include the labia majora, mons pubis, labia minora, clitoris, bulb of vestibule, vulval vestibule, greater and lesser vestibular glands, and the opening of the vagina.

In some embodiments, the present invention relates to topical therapeutic and/or prophylactic formulations for the skin, enriched in exosomes obtained from conditioned medium from cell cultures. The cells may be cultured in monolayers on conventional substrates, roller bottles, beads, or any other two-dimensional culture systems, thereby providing at least some of the many known advantages of such scalable culture systems, including precise control of the cellular microenvironment. The cells may be human to reduce the risk of an immune response and include inter alia stromal cells, keratinocytes, melanocytes, parenchymal cells, mesenchymal stem cells, neural stem cells, pancreatic stem cells and/or embryonic stem cells. In some embodiments of the present invention, monolayer cultures of primary human foreskin fibroblasts are used to condition the nutrient medium in which they are bathed. Medium conditioned by such cell cultures contain a variety of naturally secreted vesicles and proteins, including exosomes, extracellular matrix proteins and biologically active growth factors.

In embodiments, a method is disclosed including administering to a subject in need thereof a skin cream formulation derived from conditioned media containing vesicles. In a related aspect, the vesicles are exosomes. The exosomes may contain various cell-derived components such as protein, DNA, or RNA (e.g., a miRNA). In embodiments, the proteins included may be characteristic of exosomes. For example, the vesicles may contain TSG101 and CD63 proteins or the vesicles may contain CD34+ protein. Other proteins include, but are not limited to, EGF, PDGF, FGF, TGF-β, TGF-α, NGF, Epo, IGF-I, IGF-II, IL-1-α, IL-1-β, IL-2, IL-3, IL-4, IL-5, IL-6, IL-7, IL-8, IL-9, IL-10, IL-11, IL-12, IL-13, INF-α, INF-β, INF-γ, TNF-a, TNF-β, GM-CSF, and M-CSFs, or combinations thereof. Moreover, exosome compositions may comprise ALIX or PDCD6IP, RABGTpases, annexins, cytoskeletal proteins, adhesion molecules and tetraspanin family proteins. In embodiments, specific lipid compositions may be contained in said exosomes, including but not limited to, cholesterol, ceramide and sphingolipids.

In embodiments, a method of making a skin cream is disclosed including culturing a first substantially homogenous set of cells; harvesting the medium conditioned by the first set of cells; optionally, culturing a second substantially homogenous set of cells; harvesting the medium conditioned by the second set of cells; isolating exosomes from the conditioned medium of the first or second set of cells; adding the isolated exosomes to the conditioned medium from the first or second set of cells to form a conditioned medium containing an enriched population of exosomes; and adding the conditioned medium containing the enriched population of exosomes to a formulation comprising one or more solvents, a base solvent, one or more botanicals, and one or more emollients to form a cream.

Growth Factors and the Pathogenesis of Skin Aging

The dermal layer of skin contains the structural elements necessary for maintaining skin thickness, elasticity, and vitality. With age, the rate of production of these proteins decreases, and results in sagging skin and wrinkles. The secretion of extracellular proteins into conditioned medium, including growth factors, cytokines, peptides, structural and extracellular matrix proteins and precursors, and the like, presents new possibilities in the preparation of products for use in a large variety of areas including treatment and/or prevention of age-related loss of skin vitality. Growth factors are known to play important roles in promoting growth, enhancing autocrine pathways for maintenance of tissue structure and function, and in promoting wound healing. Cellular cytokines and growth factors are involved in a number of critical cellular processes including cell proliferation, adhesion, morphologic appearance, differentiation, migration, inflammatory responses, angiogenesis, and cell death. Studies have demonstrated that hypoxic stress and injury to cells induce responses including increased levels of mRNA and proteins corresponding to growth factors including inter alia, platelet-derived growth factor (PDGF), vascular endothelial growth factor (VEGF), fibroblast growth factors 1 and 2 (FGFs), insulin-like growth factors 1 and 2 (IGFs), and transforming growth factor-beta (TGF-β).

As mentioned above, some growth factors, such as TGF-β, are induced by stress proteins during wound healing. Two known stress proteins are GRP78 and HSP90. These proteins stabilize cellular structures and render the cells resistant to adverse conditions. The TGF-β family of dimeric proteins includes TGF-β1, TGF-β2, and TGF-β3 and regulates the growth and differentiation of many cell types. Furthermore, this family of proteins exhibits a range of biological effects, stimulating the growth of some cell types (Noda et al., 1989, Endocrinology 124:2991-2995) and inhibiting the growth of other cell types (Goey et al., 1989, J. Immunol. 143:877-880; Pietenpol et al., 1990, Proc. Natl. Acad. Sci. USA 87:3758-3762). TGF-β has also been shown to increase the expression of extracellular matrix proteins including collagen and fibronectin (Ignotz et al., 1986, J. Biol. Chem. 261:4337-4345) and to accelerate the healing of wounds (Mustoe et al., 1987, Science 237:1333-1335).

Another such growth factor is PDGF. PDGF was originally found to be a potent mitogen for mesenchymal-derived cells (Ross R. et al., 1974, Proc. Natl. Acad. Sci. USA 71(4); 1207-1210; Kohler N. et al., 1974, Exp. Cell Res. 87:297-301). PDGF is known to be a potent mitogen for mesenchymal stem cells, and increases the rate of cellularity and granulation in tissue formation through increased fibroblast function. Wounds treated with PDGF have the appearance of an early stage inflammatory response including an increase in neutrophils and macrophage cell types at the wound site. These wounds also show enhanced fibroblast function (Pierce, G. F. et al., 1988, J. Exp. Med. 167:974-987). Both PDGF and TGF-β have been shown to increase collagen formation, DNA content, and protein levels in animal studies (Grotendorst, G. R. et al., 1985, J. Clin. Invest. 76:2323-2329; Sporn, M. B. et al., 1983, Science (Wash DC) 219:1329). PDGF has been shown to be effective in the treatment of human wounds. In human wounds, PDGF-AA expression is increased within pressure ulcers undergoing healing. The increase of PDGF-AA corresponds to an increase in activated fibroblasts, extracellular matrix deposition, and active vascularization of the wound. Furthermore, such an increase in PDGF-AA is not seen in chronic non-healing wounds (Principles of Tissue Engineering, R. Lanza et al. (eds.), pp. 133-141 (R. G. Landes Co. Texas 1997). A number of other growth factors having the ability to induce angiogenesis and wound healing include VEGF, KGF and basic FGF.

In general, it is thought desirable in the treatment of wounds and aging skin to enhance the supply of growth factors by direct addition of these factors. Synthetic peptides, that similarly retard the aging process, may also be added to the cosmeceutical preparation. Indeed, in some cases, synthetic peptides and growth factors may be added to the culture medium in order to stimulate the cells to elaborate specific secretory proteins. Thus, the conditioned medium may include some synthetic growth factors which have not been metabolized by the cells in addition to the growth factors synthesized and secreted into the conditioned medium by the cells.

In addition, cells also produce exosomes which contain functional mRNA, miRNA, DNA, and protein molecules that may be taken up by target cells. The molecules contained in exosomes can influence target cell activation, migration, growth, differentiation or de-differentiation, or promote apoptosis or necrosis. As such, conditioned media enriched in exosomes may be used to provide additional cell factors that assist in wound healing and/or epithelial remodeling.

Cell Cultures

The pre-conditioned cell culture medium may be any cell culture medium which adequately addresses the nutritional needs of the cells being cultured. Examples of cell media include, but are not limited to Dulbecco's Modified Eagle's Medium (DMEM), Ham's F12, RPMI 1640, Iscove's, McCoy's and other media formulations readily apparent to those skilled in the art, including those found in Methods For Preparation of Media, Supplements and Substrate For Serum-Free Animal Cell Culture Alan R. Liss, New York (1984) and Cell & Tissue Culture: Laboratory Procedures, John Wiley & Sons Ltd., Chichester, England 1996, both of which are incorporated by reference herein in their entirety. In one embodiment, DMEM without phenol red is used as the cell medium. The medium may be supplemented, with any components necessary to support the desired cell or tissue culture. In a related aspect, the medium is supplemented with Antibiotic-Antimycotic and L-glutamine. In one embodiment, the Antibiotic-Antimycotic and L-glutamine each constitute 1% of the medium, and the Antibiotic-Antimycotic comprises penicillin, streptomycin sulfate, and amphotericin B. Additionally serum, such as bovine serum, which is a complex solution of albumins, globulins, growth promoters and growth inhibitors may be added if desired. The serum should be pathogen free and carefully screened for mycoplasma bacterial, fungal, and viral contamination. Also, the serum should generally be obtained from the United States and not obtained from countries where indigenous livestock carry transmittable agents. Hormone addition into the medium may or may not be desired. In one embodiment, fetal bovine serum is added to the cell medium. In a related aspect, the fetal bovine serum constitutes about 5-20% of the medium.

The ingredients of pre-conditioned media may include amino-acids (both D and/or L-amino acids) such as glutamine, alanine, arginine, asparagine, cystine, glutamic acid, glycine, histidine, isoleucine, leucine, lysine, methionine, phenylalanine, proline, serine, threonine, tryptophan, tyrosine, and valine and their derivatives; acid soluble subgroups such as thiamine, ascorbic acid, ferric compounds, ferrous compounds, purines, glutathione and monobasic sodium phosphates.

Additional ingredients include sugars, deoxyribose, ribose, nucleosides, water soluble vitamins, riboflavin, salts, trace metals, lipids, acetate salts, phosphate salts, HEPES, phenol red, pyruvate salts and buffers (see, for example, Nouricel-MD available from Melbourne Dematology, Australia).

Other ingredients often used in media formulations include fat soluble vitamins (including A, D, E and K) steroids and their derivatives, cholesterol, fatty acids and lipids Tween 80, 2-mercaptoethanol pyramidines as well as a variety of supplements including serum (fetal, horse, calf, etc.), proteins (Insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.). In one embodiment, the amphotericin B used is Fungizone.

Of course, the media may or may not need to be supplemented with growth factors, peptides, and other proteins such as attachment factors since many of the cell constructs themselves elaborate such growth and attachment factors and other products into the media.

Other ingredients for the pre-conditioned culture medium, such as vitamins, growth and attachment factors, peptides, proteins and the like, can be selected by those of skill in the art in accordance with the particular need. Embodiments of the present invention may use any cell type appropriate to achieve the desired conditioned medium.

Genetically engineered cells may be used to condition the media. Such cells can be modified, for example, to express a desired protein or proteins so that the concentration of the expressed protein or proteins in the medium is optimized for the particular desired application. In accordance with aspects of the present invention, the cells and tissue cultures used to condition the medium may be engineered to express a target gene product which may impart a wide variety of functions, including but not limited to, improved properties in expressing proteins resembling physiological reactions, increased expression of a particular protein useful for a specific application, such as wound healing or inhibiting certain proteins such as proteases, lactic acid, and the like.

The medium may be conditioned by stromal cells, keratinocytes, melanocytes, parenchymal cells, mesenchymal stem cells (lineage committed or uncommitted progenitor cells), liver reserve cells, neural stem cells, pancreatic stem cells, and/or embryonic stem cells. The cells may include, but are not limited to, bone marrow, skin, liver, pancreas, kidney, neurological tissue, adrenal gland, mucosal epithelium, and smooth muscle, to name but a few. The fibroblasts and fibroblast-like cells and other cells and/or elements that comprise the stroma may be fetal or adult in origin, and may be derived from convenient sources such as skin, liver, pancreas, mucosa, arteries, veins, umbilical cord, and placental tissues, and the like. Such tissues and/or organs can be obtained by appropriate biopsy or upon autopsy. In fact, cadaver organs may be used to provide a generous supply of stromal cells and elements.

In addition, exosome production may be induced/enhanced in such cells by cytokine/mitogen exposure, uptake of latex beads, $Ca^{+2}$ exposure, hypoxia, or other manipulations of the cell culture (e.g., apoptosis induction). In embodiments, increased exosome production from cell cultures may be accomplished by using the Integra CELLine® Culture System (see, e.g., Mitchell et al., J Immunol Methods., 335 (1-2):98-105, 2008).

Fibroblasts may be readily isolated by disaggregating an appropriate organ or tissue which is to serve as the source of the fibroblasts. This may be accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase, and the like. Mechanical disruption can also be accomplished by a number of methods including, but not limited to, the use of grinders, blenders, sieves, homogenizers, pressure cells, or insonators to name but a few. For a review of tissue disaggregation techniques, see Freshney, Culture of Animal Cells: A Manual of Basic Technique, 2d Ed., A. R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, Culture of Animal Cells: A Manual of Basic Techniques, 2d Ed., A. R. Liss, Inc., New York, 1987, Ch. 11 and 12, pp. 137-168.

The isolation of fibroblasts may, for example, be carried out as follows: fresh tissue samples (e.g., human foreskin) are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency. In one aspect, deposit of viable human fibroblast cells designated AQHFF-0 has been made with the American Type Culture Collection ("ATCC"), 10801 University Blvd., Manassas, Va. on Feb. 14, 2011, having ATCC Accession No. PTA-11681.

In another aspect, the fibroblast cells are transformed with SV40 Large T antigen to establish long term immortalized cultures. In a related aspect, deposit of viable transformed human fibroblast cells designated AQHFF-SV40 has been made with the American Type Culture Collection ("ATCC"), 10801 University Blvd., Manassas, Va. on Feb. 14, 2011, having ATCC Accession No. PTA-11680.

The deposits were made in accordance with the terms and provisions of the Budapest Treaty. All restrictions on the availability to the public of the materials so deposited will be irrevocably removed upon the granting of the patent. The cells will be maintained for a term of at least thirty (30) years and at least five (5) years after the most recent request for the furnishing of a sample of the deposit is received by the depository, and at least beyond the enforceable life of the patent(s) for which the deposit was made, whichever is longer.

Embryonic stem cells and/or other elements that comprise the stroma may be isolated using methods known in the art. For instance, human embryonic stem cell populations and methods for isolating and using these cells have been reported in Keller et al., Nature Med., 5:151-152 (1999), Smith Curr. Biol. 8:R802-804 (1998); isolated from primordial germ cells, Shamblatt et al., PNAS 95:13726-1373 (1998); isolated from blastocytes, Thomason et al., Science 282:1145-1147 (1988). The isolation and culture of mesenchymal stem cells are known in the art. See Mackay et al., Tissue Eng. 4:415-428 (1988); William et al., Am Surg. 65:22-26 (1999). Likewise, neural stem cells may be isolated in the manner described in Flax et al., Nature Biotechnol., 16:1033-1039 (1998); and Frisen et al., Cell. Mol. Life Sci., 54:935-945 (1998).

The cells can be cultured in accordance with disclosed embodiments by any means known in the art, including in monolayer and beads and by any means (i.e., culture dish, roller bottle, a continuous flow system, etc.). In one aspect, the cells are cultured in an environment which enables aseptic processing and handling. Conventional means of cell and tissue culture have been limited by the need for human supervision and control of the media. This limits the amount of cells and tissue that can be cultured at a single time and consequently the volume of conditioned cell media that can be obtained at a single time. For this reason, the media may be conditioned in a manner allowing for large scale growth (yielding large scale conditioned media). In another aspect, cells may be arrested in growth phase by irradiation or mytomycin-c treatment to reduce the need for human supervision.

In some embodiments, the cells to be cultured may be first plated on dishes, then on flasks, then on two-liter roller bottle systems. Once a sufficient number of cells has been grown, the cells may be passaged to two-dimensional flat hexagonal shaped polysterene microcarriers. In one embodiment, the polystyrene microcarriers are Nunc 2D MicroHex carriers. In one aspect, microcarriers, with attached cells, may be suspended in ten-liter capacity bioreactors, which consist of a disposable sterile plastic bag placed on top of a rocker system. Each bag is expected to generate media for approximately 3 months before the cells are spent. When the media is subsequently collected, it may be filtered to remove any cells that may be present. The media may also be concentrated or diluted with PBS or $dH_2O$ to modify the growth factor concentrations. Corning 75 $cm^2$ tissue culture flasks may be used. Batches may be tested for growth factor/cytokine content through Upstate Labs Beadlyte Human Cytokine Profiler testing services using Luminex technology.

See also "What is preferred method for cell culture?": The Wave Bioreactor (System 20/50, Wave Biotech, New Jersey) in which cell culture (0.1-25 L volume) may be performed in pre-sterile, single use plastic bags. The bag may be filled with media, cells, and Nunc microcarriers and inflated to form a rigid gas-impermeable chamber. It may then placed on a rocking platform and rocked to induced waves. The gentle wave motion provides oxygenation and mixing of the media with minimal shear force.

The culturing of cells may be done on a laboratory scale or an industrial pilot or production scale. Scale up may be accomplished using commercially available products and technologies, e.g., Nunc Brand Products, including, Nunclon™ A surface across the range (from small single well to the Cell Factory 40 (CF40). Harvesting and clean up of secreted products may take place using conventional techniques.

In addition to the broad range of available surfaces and surface area configurations, particles may also be used in fermenters that support the growth of cells in stirred suspensions. Two-dimensional microcarriers (e.g., MICROHEX™ from Nunc) are hexagonal two-dimensional low-density particles requiring minimal stirring and therefore subjecting cells to minimal stress.

Traditional barriers to large-scale mammalian culture have now been addressed, with stirred-tank reactors emerging as one of industry's technology of choice. The issues of adapting cells to suspension culture, shear sensitivity and oxygen supply have been largely resolved. But for many low-volume and specialty applications, reactor technology remains diversified, with reactor types ranging from roller bottles to stacked plates and hollow fibers.

In general, where cell lines, as opposed to primary cultures, are utilized, they are preferably screened for human and animal pathogens. Depending upon the application, such screening may be more or less important, e.g., in wound healing or food additive applications, where pathogen free cells are desirable. Methods of screening for pathogens are well known in the art. The cell type will affect the properties of the conditioned medium.

A few researchers have explored the use of natural substrates related to basement membrane components. Basement membranes comprise a mixture of glycoprotein and proteoglycans that surround most cells in vivo. For example, Reid and Rojkund, 1979, In, Methods in Enzymology, Vol. 57, Cell Culture, Jakoby & Pasten, eds., New York, Acad. Press, pp. 263-278; Vlodaysky et al., 1980, Cell 19:607-617; Yang et al., 1979, Proc. Natl. Acad. Sci. USA 76:3401 have used collagen for culturing hepatocytes, epithelial cells and endothelial tissue. Growth of cells on floating collagen (Michalopoulos and Pitot, 1975, Fed. Proc. 34:826) and cellulose nitrate membranes (Savage and Bonney, 1978, Exp. Cell Res. 114:307-315) have been used in attempts to promote terminal differentiation.

Cultures of mouse embryo fibroblasts have been used to enhance growth of cells, particularly at low densities. This effect is thought to be due partly to supplementation of the medium but may also be due to conditioning of the substrate by cell products. In these systems, feeder layers of fibroblasts are grown as confluent monolayers which make the surface suitable for attachment of other cells. For example, the growth of glioma on confluent feeder layers of normal fetal intestine has been reported (Lindsay, 1979, Nature 228:80).

Stromal cells may be genetically engineered to adjust the level of protein products secreted into the culture medium to improve the concentration of recovered product obtained from the conditioned medium. For example, anti-inflammatory factors, e.g., anti-GM-CSF, anti-TNF, anti-IL-1, anti-IL-2, and the like. Alternatively, stromal cells may be genetically engineered to "knock out" expression of native gene products that promote inflammation, e.g., GM-CSF, TNF, IL-1, IL-2, or "knock out" expression of MHC in order to lower the risk of rejection. The cells used to condition the medium may be genetically modified to alter the concentration of proteins found in the medium. The conditioned cell medium is processed for uses which include cosmetic additives and any pharmaceutical applications related to topical formulations for treatment and/or prevention of aging, wrinkles, and wound healing. In one embodiment, compositions and methods are disclosed for stimulating hair growth, including stimulation of hair growth on the head and eyelashes. In some embodiments, the invention also relates to compositions containing extracellular matrix proteins and/or other purified protein(s) derived from the conditioned medium.

The cells may be engineered to express a target gene product which is biologically active and provides a chosen biological function, which acts as a reporter of a chosen physiological condition, which augments deficient or defective expression of a gene product, or which provides anti-viral, anti-bacterial, anti-microbial, or anti-cancer activity. In accordance with the present invention, the target gene product may be a peptide or protein, such as an enzyme, hormone, cytokine, antigen, or antibody, a regulatory protein, such as a transcription factor or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may up-regulate an endogenous protein, introduce a new protein or regulate ion concentration by expressing a heterologous ion channel or altering endogenous ion channel function. Examples include, but are not limited to engineered tissues that express gene products which are delivered systemically (e.g., secreted gene products such as proteins including growth factors, hormones, Factor VIII, Factor IX, neurotransmitters, and enkaphalins).

Methods for preparing DNA constructs containing the gene of interest, for transforming or transfecting cells, and for selecting cells carrying and expressing the gene of interest are well-known in the art. See, for example, the techniques described in Maniatis et al., 1989, Molecular Cloning, A Laboratory Manual, Cold Spring Harbor Laboratory Press, Cold Spring Harbor, N.Y.; Ausubel et al., 1989, Current Protocols in Molecular Biology, Greene Publishing Associates & Wiley Interscience, N.Y.; and Sambrook et al., 1989, Molecular Cloning: A Laboratory Manual, 2nd Ed., Cold Spring Harbor Laboratory Press, Cold Spring Harbor, N.Y.

The cells can be engineered using any of a variety of vectors including, but not limited to, integrating viral vectors, e.g., retrovirus vector or adeno-associated viral vectors; or non-integrating replicating vectors, e.g., papilloma virus vectors, HSV vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection. In one aspect of the present invention, the cells are transformed with an SV40 Large T Antigen containing vector to establish immortalized cells. In a related aspect, the vector is an SV40 Large T (SVLT) antigen mammalian expression vector, where such a vector contains and proximal SVLT promoter and distal SVLT element which flank the SV Large T antigen encoding sequence, one or more bacteriophage promoters, one or more multiple cloning sites, one or more bacterial cell selection genes, one or more mammalian cell selection genes, one or more sites for integration into a mammalian host, or one or more elements for plasmid propagation/replication in bacterial hosts, or a combination thereof. For example, the vector may be pBsSVD2005 (AddGene, Cambridge Mass.). See, e.g., FIG. 1.

The cells are preferably transformed or transfected with a nucleic acid, e.g., DNA, controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, may be cloned and expanded into cell lines. This method may be advantageously used to engineer cell lines which express the gene product into the media.

Any promoter may be used to drive the expression of the inserted gene. For example, viral promoters include but are not limited to the CMV promoter/enhancer, SV40, papillomavirus, Epstein-Barr virus, elastin gene promoter and B-globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters may be used to drive the expression of the inserted gene when necessary. Inducible promoters may be built into integrating and/or replicating vectors. For example, inducible promoters include, but are not limited to, metallothionein and heat shock protein.

According to one embodiment, the inducible promoters used for expressing exogenous genes of interest are those that are the native promoters of those regulatory proteins as disclosed herein that are induced as a result of cyropreservation and subsequent thawing. For example, the promoter of TGF-B, VEGF, or various known heat shock proteins may be used as the expression control element, i.e., may be operatively linked to an exogenous gene of interest in order to express a desired gene product in the tissue constructs conditioning the cell media.

A variety of methods may be used to obtain the constitutive or transient expression of gene products engineered into the cells. For example, the transkaryotic implantation technique described by Seldon et al., 1987, Science 236:714-718 may be used. "Transkaryotic", as used herein, suggests that the nuclei of the implanted cells have been altered by the addition of DNA sequences by stable or transient transfection. In one aspect, the cells may be engineered to express such gene products transiently and/or under inducible control during the post-operative recovery period, or as a chimeric fusion protein anchored to the stromal cells, for example, as a chimeric molecule composed of an intracellular and/or transmembrane domain of a receptor or receptor-like molecule, used to the gene product as the extracellular domain.

In other aspects of the present invention, the two-dimensional tissue cultures which condition the cell media may contain fibroblasts, keratinocytes, melanocytes, mesenchymal stem cells, liver reserve cells, neural stem cells, pancreatic stem cells, and/or embryonic stem cells and/or parenchymal cells and/or parenchymal stem cells found in many tissue types, including but not limited to bone marrow, skin, liver, pancreas, kidney, adrenal and neurologic tissue, as well as tissues of the gastrointestinal and genitourinary tracts, and the circulatory system. See e.g., U.S. Pat. Nos. 4,721,096; 4,963,489; 5,032,508; 5,266,480; 5,160,490; and 5,559,022, each of which is incorporated by reference herein in its entirety.

In other embodiments, different cell types may be cultured separately, wherein conditioned medium enriched with different cell type-specific factors may be formulated by mixing desired proportions of media conditioned by these different cell types. Such individual two-dimensional culturing may employ any of the above-mentioned cell types including genetically engineered cells and cell lines.

Conditioned Medium

A novel approach to reverse the effects of skin aging and eliminate facial wrinkles was proposed by Naughton et al., in U.S. Pat. No. 6,372,494 (incorporated in its entirety herein by reference). Applicants now improve on the Naughton methods to re-establish the natural environment of nascent skin by delivering critical structural proteins and relevant growth factors directly to the skin. This may be accomplished by combining growth factor-enriched conditioned medium from one or more cell types grown independently under highly controlled monolayer (two-dimensional) culture conditions, with a formulated cosmeceutical preparation, e.g., a cream, salve, gel, lotion, spray, serum, and the like. In addition to the conditioned medium, the cosmeceutical preparation preferably comprises one or more of a variety of other beneficial active and inert ingredients that are used with efficacy in the field.

In one embodiment, the homogeneous growth factor-enriched conditioned medium from a single cell type is employed in the skin cream formulation. In other variations, the conditioned media from different cell types are mixed to provide optimal growth factor and secreted structural protein constituents.

In some embodiments, the growth factor-rich conditioned media may be diluted, concentrated and/or preserved prior to combining it with the variety of formulations for varying topical applications, such as facial serum, eye cream, dermal repair cream, self-tanning lotion, and the like. Concentration may be accomplished by any conventional methods known in the art, including for example, freeze-drying, vacuum-drying, evaporation, and the like. Moreover, particular growth factors may be concentrated by affinity chromatography or other conventional methods for protein/peptide purification. Dilution methods may include addition of deionized water. Preservation methods may include inter alia, freeze-drying, spray-drying, foam-drying, and the like. In one embodiment, the medium is filtered with a 7 micron filter, then preservatives and other ingredients and/or supplements are added to the medium, and the medium is stored in a refrigerator. In addition, the conditioned medium may be subjected to further processing, e.g., affinity chromatography, to differentially concentrate or remove certain medium components, as detailed below.

Following removal of the cell conditioned medium, it may be necessary to further process the resulting supernatant. Such processing may include, but is not limited to, centrifugation, product isolation and purification, dilution of the media or concentration of the media by a water flux filtration device or by defiltration using the methods described in Cell & Tissue Culture: Laboratory Procedures, supra, pp 29 D:0.1-29D:0.4.

The conditioned medium may be further processed for product isolation and purification to remove unwanted proteases, for example. The methods used for product isolation and purification so that optimal biological activity is maintained will be readily apparent to one of ordinary skill in the art. For example, it may be desirous to purify a growth factor, regulatory factor, peptide hormone, antibody, or the like. Such methods include, but are not limited to, gel chromatography (using matrices such as Sephadex) ion exchange, metal chelate affinity chromatography with an insoluble matrix such as cross-linked agarose, HPLC purification and hydrophobic interaction chromatography of the conditioned media. Such techniques are described in greater detail in Cell & Tissue Culture; Laboratory Procedures, supra. Of course, depending upon the desired application of the conditioned medium, and/or products derived thereof, appropriate measures must be taken to maintain sterility. Alternatively, sterilization may be necessary and can be accomplished by methods known to one of ordinary skill in the art, such as, for example, heat and/or filter sterilization taking care to preserve the desired biological activity.

In one embodiment, the media is filtered or centrifuged to prevent cell inclusion. It may then be diluted, e.g., with PBS or deionized water, if the growth factor concentrations are too high. Alternatively, the conditioned medium may be concentrated if the growth factor levels are not sufficiently high. The diluted or concentrated media may then be combined with the cream/gel formulation.

As previously mentioned, the conditioned medium contains numerous products which may be concentrated. For example, human dermal fibroblasts synthesize and secrete collagen precursors and a fraction of these precursors are incorporated into the extracellular matrix. This incorporation requires the removal of terminal peptides (N- and C-peptides) which significantly lowers the solubility of the collagen molecules (the rest of the secreted collagen remains in solution due to lack of proteolysis). Generally, soluble collagen may be obtained under neutral pH conditions at high salt concentrations. See Kielty, C. M., I. Hopkinson, et al. (1993), Collagen: The Collagen Family: Structure, Assembly, and Organization in the Extracellular Matrix, Connective Tissue and Its Heritable Disorders: molecular, genetic and medical aspects. P. M. Royce and B. Steinmann New York, Wiley-Liss, Inc.: 103-149).

It should be understood that the following protocol is offered by way of example and may be modified using methods known to those of skill in the relevant art: To purify the collagen, add 240 ml of medium conditioned with fibroblasts to 240 ml 5M NaCl (a 1:1 ratio of medium to salt) and precipitate for 16 hours at 4° C. Centrifuge the suspension for approximately 20 minutes at 4000×g. Discard the supernatant. Wash the pellet with 10 ml of a solution of 50 mM Tris-HCl (pH 7.5) and 2.4M NaCl. Centrifuge for 20 minutes at 4000×g and discard the supernatant. Resuspend the pellet in 10 ml of 0.5M acetic acid. To remove the propeptides, add 0.1 ml of pepsin (100 mg/mL) (Sigma Chemical, St. Louis, Mo.) and digest for 16 hours at 4° C. (this removes the propeptides but leaves the triple helix intact). Centrifuge the suspension for 20 minutes at 4000×g. Recover supernatant and discard the pellet. Add 2.1 ml of 5M NaCl and 0.5M acetic acid to a final volume of 15 ml (final NaCl concentration of 0.7M). Precipitate for approximately 16 hours at 4° C. Centrifuge the suspension for 20 minutes at 4000×g and discard the supernatant. Dissolve pellet in 0.5 ml of 0.5M acetic acid solution. The purity of the collagen should be at least 90% and may be analyzed by standard methods known in the art such as SDS-PAGE, for example.

The conditioned medium compositions may be comprised of any known defined or undefined medium and may be conditioned using any eukaryotic cell type. The medium may be conditioned by stromal cells, keratinocytes, melanocytes, parenchymal cells, mesenchymal stem cells, liver reserve cells, neural stem cells, pancreatic stem cells, and/or embryonic stem cells. The cell type will affect the properties of the conditioned medium. For example, a medium conditioned with astrocytes and neuronal cells will elaborate certain characteristic metabolites and proteins so that such a conditioned medium is preferred for certain nerve repair applications. The cell culture may further be cultured with parenchymal cells such as the cells of the skin, bone, liver, nerve, pancreas, etc., resulting in a conditioned medium containing characteristic extracellular proteins and other metabolites of that tissue type. Accordingly, in accordance with one embodiment of the present invention, media conditioned by different cell types may be mixed in different proportions to provide a formulation adapted to deliver a combination of cell or tissue-specific conditioning characteristics. For example, in one embodiment of a skin cream, conditioned medium from fibroblast cultures (rich in the peptide growth factors and extracellular proteins used in maintaining a healthy dermal microenvironment) may be combined with an amount of conditioned medium from keratinocyte cultures (rich in the extracellular proteins and other metabolites characteristic of the keratin-forming epidermal tissues). Indeed, in some embodiments, conditioned medium from cell cultures representing a variety of different tissues may be formulated for addressing particular cosmeceutical applications (e.g., age-related decrements in connective and elastic matrices, blotchy pigmentation and facial muscle tone).

Additionally, each cell type may also be genetically modified as detailed above. The genetic modification may be used to alter the concentration of one or more component in the medium such as, for example, to upregulate a protein, to introduce a new protein, or to regulate ion concentration. Further, cells including heterogeneous primary cell cultures and/or cell lines may be cloned, mutated, and/or selected for desired phenotype, genotype, responsiveness to culture conditions (e.g., temperature, pH, pharmacologic agents, etc.), protein secretory characteristics, and the like.

Exosomes

After conditioned media is isolated, exosomes may be extracted from media by methods know in the art (see, e.g., Taylor et al., Methods in Mol. Biol. 728:235-246, 2011).

In embodiments, the conditioned media may be centrifuged at 12,000×g for about 15 min. at about 4° C. (low speed centrifugation). The resulting supernatant may then be centrifuged at 100,000×g for about 1 hr at about 4° C. The resulting pellet may then be re-suspended in 4° C. phosphate buffered saline (i.e., PBS; other physiological buffers may be used), and the re-suspended material may then be re-centrifuged for 1 hr at 100,000×g, 4° C., and resuspended in PBS until use.

In embodiments, the exosomes may be isolated by column chromatography. As stated above, the conditioned media may be centrifuged at 12,000×g for about 15 min. at about 4° C. After low speed centrifugation, an aliquot of the supernatant (e.g., 2-3 ml) is applied to a 2% agarose based gel column (2.5×16 cm). For optimum separation, the sample volume should be about 1/20 of the total column volume (as defined by $\pi r^2 h$). The material may then be eluted isocratically with PBS at a flow rate of about 1 ml/min, monitoring the eluate at 280 nm, where fractions are collected (2-3 ml). The void volume fractions are pooled, and centrifuged at 100,000×g for 1 hr at 4° C., where the pelleted exosomes may be recentrifuged after suspension in PBS, and finally resuspended in PBS until use.

Alternatively, populations of exosomes may be enriched by absorption to antibody conjugated magnetic microbeads. For example, anti-surface-antigen Ab-magnetic beads (about 50 µl) may be mixed with about 2 ml of low speed centrifugation conditioned media supernatant, and incubated on a shaker at room temperature. After a sufficient time (about 2 hrs), tubes containing the immune complexes are place in a magnetic separator, the fluid is removed, leaving the magnetic beads (mb) and bound exosomes attached to the side of the tubes. The tubes may then be removed from the magnetic separator, where the beads are rinsed with about 500 µl of Tris buffered saline (although other buffers may be used) and the separation repeated. The isolated exosomes/microbeads may be diluted in IgG elution buffer (Pierce Chemical Co, Rockford, Ill.) and the complex centrifuged at about 10,000 rpm (low speed centrifuge) to separate the microbeads from the exosomes (supernatant). The supernatant may then be centrifuged at 100,000×g for about 1 hour at 4° C. The pelleted exosomes may then be resuspended in about 250 µl phosphate-buffered saline (PBS).

Other methods include the use of EXOQUICK™ (available from System Biosciences Inc, Mountain View, Calif.; see Taylor et al. (2011), supra) polymer based precipitation methods. Typical exosome yields from cell culture may be from about 0.5 to about 0.7 µg/ml culture, about 0.7 to about 1.0 µg/ml culture, about 1.0 to about 2.0 µg/ml culture, about 2.0 to about 4.0 µg/ml culture or about 4.0 to about 10.0 µg/ml culture.

Once isolated, the exosomes may be analyzed for protein/RNA analysis or may be used to form topical formulations such as creams, lotions, serums, or hydrogels to reduce or eliminate wrinkles, frown lines, increase eyelash growth, reduce scarring and to repair other skin conditions, including but not limited to vaginal rejuvenation. In a related aspect, the formulations may contain about 5-40% conditioned medium, about 10-38% conditioned media, about 25-35% conditioned media, where the conditioned medium contains at least about a 20% increase in exosomes, about a 40% increase in exosomes, about a 50% to about a 100% increase in exosomes, about a 1.5 fold increase in exosomes, about 1.5 to about 2.5 fold increase in exosomes, about 2.5 to about 3.5 fold increase in exosomes, about 3.5 to about 4.5 fold increase in exosomes, about 5 fold increase in exosomes or about a 10 fold increase in exosomes compared to non-enriched conditioned media.

Commercial Applications

In embodiments, injectable formulations comprising the growth factor/exosome-enriched conditioned medium may be used in cosmetic applications, similar to the use of BOTOX®. Indeed, the growth factor/exosome-enriched conditioned medium may be used in combination with other injectable agents to provide enhanced treatment of aging skin. In other embodiments, the conditioned medium may also be added to eye shadow, pancake makeup, compacts or other cosmetics. In other embodiments, the compositions of the invention may be formulated for topical applications for stimulating hair growth on the head and eyelashes.

In other embodiments, the growth factor/exosome-enriched conditioned medium may be used as food additives and dietary supplements. Preferably, the conditioned medium contains a variety of nutrients, including essential amino acids, vitamins, and minerals, which were present in fresh culture medium prior to exposure to the cells, and remain present at significant and beneficial levels. The conditioned media of the invention may be concentrated and/or lyophilized, for example, and may be administered as dietary supplements in the form of capsules or tablets for ingestion. Additionally, the compositions may also be added directly to food to enhance its nutritional content in liquid or powdered form. In some of these embodiments, the conditioned medium formulations may be supplemented with conventional nutritional supplements, e.g., vitamins, minerals, amino acids, polysaccharides, antioxidants, antibiotics, etc.

In yet another embodiment of the invention, the growth factor/exosome-enriched conditioned medium may be used to supplement cell culture medium—for growing other cells in culture. The conditioned media of the invention contain factors useful in promoting cell attachment and growth. Further, the cell medium may be conditioned by cells which are genetically engineered and which may, for example, contain increased fibronectin or collagen concentrations beneficial in promoting cell attachment to a scaffold or culture surface.

In an additional embodiment of the invention, the growth factor/exosome-enriched conditioned medium may be used for pharmaceutical applications, e.g., as a source of specific growth factors or other proteins having pharmaceutical utility. As discussed above, the specific factors of interest may be differentially concentrated and/or purified by conventional methods, such as affinity chromatography. As such, the conditioned media of the invention may be beneficial for a variety of pharmaceutical applications.

In yet other embodiments, the conditioned medium of the invention may be used in wound and/or burn healing. Indeed, wounded, sun-damaged, burned, and aging skin may share many pathological features. Thus, the following descriptions of uses of the growth factor/exosome-enriched conditioned media in wound healing may also be applicable to sun damaged, burned and aging skin. Examples of uses of the growth factor/exosome-enriched conditioned medium include, but are not limited to, applying the conditioned medium to the gauze of a bandage (adhesive or non-adhesive) and used in topical applications to promote and/or accelerate wound healing. The conditioned medium may be processed to concentrate or reduce one or more components to enhance wound healing. The compositions may be lyophilized/freeze-dried and added as a wound filler or added to existing wound filling compositions to accelerate wound healing. Alternatively, the medium may be added to a hydrogel composition and used as a film for topical wound treatments and anti-adhesion applications. The growth factor/exosome-enriched conditioned medium may be generated by cells which express gene products with improved wound-healing properties; i.e., engineered cells which express gene products that have anti-scarring properties.

When skin tissue is physically insulted, polypeptide growth factors, which exhibit an array of biological activities, are released into the insulted area to promote healing. Wound healing is a complex process that involves several stages and is capable of sealing breaches to the integument in a controlled manner to form functionally competent tissue. The process begins with hemostasis followed by an inflammatory phase involving neutrophils and macrophages. The process continues with the development of granulation tissue and re-epithelialization to close the wound. Subsequently, scar tissue forms and is remodeled over the succeeding months to an approximation of the original anatomical structure. Ideally, scar tissue is minimal so that healthy tissue, functionally competent tissue which histologically and physiologically resembles the original normal tissue, may form. Each stage of the healing process is controlled by cellular interactions through regulatory proteins such as cytokines, growth factors, and inflammatory mediators as well as cell contact mechanisms. For example, inflammatory mediators such as IL-6, IL-8, and G-CSF induce lymphocyte differentiation and acute phase proteins, as well as neutrophil infiltration, maturation and activation, processes that are important in the inflammatory stages of wound healing. Other examples of regulatory proteins involved in the wound healing process are VEGF that induces angiogenesis during inflammation and granulation tissue formation, the bone morphogenetic proteins (BMPs) which induce bone formation, keratinocyte growth factor (KGF) that activates keratinocytes, and TGF-$\beta$ that induces deposition of extracellular matrix.

In chronic wounds, the healing process is interrupted at a point subsequent to hemostasis and prior to re-epithelialization, and is apparently unable to restart. Most of the inflammation seen in the wound bed is related to infection, but the inflammation gives rise to an environment rich in proteases that degrade regulatory proteins and thus interfere with the wound healing process. Similarly, in some medical conditions, such as diabetes, some of the regulatory proteins needed for wound healing are in short supply. For example, it has been found in a mouse model of non-insulin-dependent diabetes (e.g., the db/db mouse) that secretion of VEGF and PDGF and expression of the PDGF receptor are all depressed in wounds compared to the levels in wounds of normal mice.

Thus, the growth factor/exosome-enriched conditioned media of the present invention contain many of the regulatory proteins thought to be important in wound healing and which have been shown to be depleted in vivo models of wound healing. Similarly, the conditioned medium may also be useful in the treatment of other types of tissue damage, e.g., traumatic or congenital, wherein the repair and/or regeneration of tissue defects or damage is desired since many of these growth factors may be present in the conditioned cell medium, depending on the cell types used to condition the medium, including, for example, FGFs, PDGFs, EGFs, BMPs, VEGF, KGF and TGFs. Stress proteins, such as GR 78 and MSP90 induce local secretion of growth factors such as TGF-$\beta$. TGF-$\beta$, including TGF $\beta$-1, TGF $\beta$-2, TGF $\beta$-3, TGF $\beta$-4 and TGF $\beta$-5 (and may be used in the culture medium to upregulate the levels of these TGFs in the conditioned medium), regulate growth and differentiation, and accelerate wound healing (Noda et al. 1989, Endocrin. 124: 2991-2995; Goey et al. 1989, J. Immunol. 143: 877-980, Mutoe et al.

1987, Science 237: 1313-1335). Mitogens, such as PDGF increase the rate of cellularity and granulation in tissue formation (Kohler et al. 1974, Exp. Cell. Res. 87: 297-301). As previously mentioned, the cells are preferably human to minimize immunogenicity problems.

In one aspect, a combination of the growth factors and conditioned media includes TGF Beta-1, TGF Beta-2, TGF Beta-3, IL-3, IL-6, IL-7, and IL-8, where the conditioned media is present at a concentration of at least 20% (wt %). In a related aspect, the combination includes about 1-3 ng/mL TGF Beta-1, about 100-160 pg/mL TGF Beta-2, about 50-100 pg/mL TGF Beta-3, about 60 pg/mL IL-3, about 11 pg/mL IL6, about 50 pg/ML IL-7, and about 4-10 pg/mL IL-8, and where the conditioned media is present at about 30-42% (wt %).

Because the conditioned medium contains such an array of wound healing factors, the conditioned medium may be employed advantageously in the treatment of wound and burn healing including skin wounds, broken bones, gastric ulcers, pancreas, liver, kidney, spleen, blood vessel injuries and other internal wounds. Further, the conditioned medium may be combined with other active agents such as antibiotics and analgesics. Embodiments include formulations of the conditioned media with a salve or ointment for topical applications.

Alternatively, as discussed above, the conditioned medium may be combined with a bandage (adhesive or non-adhesive) to promote and/or accelerate wound healing. The conditioned media may be used in any state, i.e., liquid or solid, frozen lyophilized or dried into a powder, as a film for topical wound treatments and anti-adhesion applications, or as an injectable; see PCT WO 96/39101, incorporated herein by reference in its entirety.

Alternatively, the conditioned cell medium may be formulated with polymerizable or cross-linking hydrogels as described in U.S. Pat. Nos. 5,709,854; 5,516,532; 5,654,381; and WO 98/52543, each of which is incorporated herein by reference in its entirety. Examples of materials which can be used to form a hydrogel include modified alginates. Alginate is a carbohydrate polymer isolated from seaweed, which can be cross-linked to form a hydrogel by exposure to a divalent cation such as calcium, as described, for example in WO 94125080, the disclosure of which is incorporated herein by reference. Alginate is ionically cross-linked in the presence of divalent cations, in water, at room temperature, to form a hydrogel matrix. As used herein, the term "modified alginates" refers to chemically modified alginates with modified hydrogel properties.

Additionally, polysaccharides which gel by exposure to monovalent cations, including bacterial polysaccharides, such as gellan gum, and plant polysaccharides, such as carrageenans, may be cross-linked to form a hydrogel using methods analogous to those available for the cross-linking of alginates described above.

Modified hyaluronic acid derivatives may also be useful. As used herein, the term "hyaluronic acids" refers to natural and chemically modified hyaluronic acids. Modified hyaluronic acids may be designed and synthesized with preselected chemical modifications to adjust the rate and degree of cross-linking and biodegradation.

Covalently cross-linkable hydrogel precursors also are useful. For example, a water soluble polyamine, such as chitosan, can be cross-linked with a water soluble diisothiocyanate, such as polyethylene glycol diisothiocyanate.

Alternatively, polymers may be utilized which include substituents which are cross-linked by a radical reaction upon contact with a radical initiator, such as those disclosed in Naughton et al. U.S. Pat. No. 6,372,494; incorporated herein in its entirety by reference.

In yet another embodiment, the conditioned medium, and/or particular conditioned medium concentrates, e.g., extracellular matrix proteins elaborated into the media, may be used to coat sutures. The naturally secreted extracellular matrix may provide the conditioned media with type I and type III collagens, fibronectin, terascin, glycosaminologycans, versican, decorin and various other secreted human dermal matrix proteins, as well as the variety of growth factors discussed above that are involved in orchestrating assembly of dermal tissues from the extracellular matrix and cellular building blocks. Similarly, the conditioned cell media or the extracellular matrix proteins derived from the conditioned media may be used to coat conventional implantation devices, including vascular prosthesis, in surgical approaches to correct defects in the body, resulting in superior implantation devices. The implants should be made of biocompatible, inert materials that replace or substitute for the defective function and are either non-biodegradable or biodegradable. By coating implantation devices with medium containing these extracellular proteins and growth factors, the implant invites proper cellular attachments resulting in superior tissue at the implantation site. Thus, sutures, bandages, and implants coated with conditioned cell medium, or proteins derived from the medium, enhance the recruitment of cells, such as leukocytes and fibroblasts into the injured area and induce cell proliferation and differentiation resulting in improved wound healing.

In yet another embodiment, the medium may be formulated with a pharmaceutically acceptable carrier as a vehicle for internal administration. Also, the medium may be further processed to concentrate or reduce one or more factor or component contained within the medium, for example, enrichment of a growth factor using immunoaffinity chromatography or, conversely, removal of a less desirable component, for any given application as described herein.

Of course, wounds at specialized tissues may require medium conditioned by that specialized tissue. For example, injuries to neuronal tissues may require proteins contained in medium conditioned by neuronal cell cultures. Specific products may be derived, or alternatively, the conditioned medium may be enriched by immunoaffinity chromatography or enhanced expression of a desired protein from the specific medium such as, for example, NGF. NGF-controlled features include, but are not limited to, the cholinergic neurotransmitter function (acetylcholinesterase (AChE) and the acetylcholine-synthesizing enzyme (ChAT)), neuronal cell size, and expression of Type II NGF receptors; NGF is secreted into the conditioned medium conditioned by glial and other neuronal cells, which can then be used in a composition for nerve healing.

Deficits of endogenous NGF may aggravate certain human neurodegenerative disorders and there is an apparent inability of injured adult CNS neurons to regenerate. Specifically, injury to a nerve is followed by degeneration of the nerve fibers distal to the injury, the result of isolation of the axon from the cell body. In the central nervous system, there is no significant growth at the site of injury typically leading to death of the damaged neuron. NGF plays a crucial role in the regenerative capabilities of adult CNS cholinergic neurons at the cell body level (e.g. septum), the intervening tissue spaces (e.g., nerve bridge) and the reinervation area (e.g., hippocampal formation). Additionally, NGF may be beneficial in improving cognitive defects. Medium conditioned with glial cells for example, can supply exogenous NGF and other nerve growth factors so that new axons can grow out from the cut ends of the injured nerve (e.g., develop a growth cone) elongating to the original site of the connection.

Further, injury to the brain and spinal cord is often accompanied by a glial response to the concomitant axonal degeneration, resulting in scar tissue. This scar tissue was initially thought to be a physical barrier to nerve growth, however, of greater significance is the presence or absence of neuronotropic factors in the extra neuronal environment. Astrocytes appear to be capable of synthesizing laminin in response to injury (laminin can also be found in the conditioned media). Collagen and fibronectin, and especially laminin have been found to promote the growth of neurities from cultured neurons or neuronal explants in vitro. These extracellular matrix proteins appear to provide an adhesive substratum which facilitates the forward movement of the growth cone and elongation of the axon. Thus, the presence of neuronotropic factors and a supportive substratum may be required for successful nerve regeneration since regeneration appears to require that: the neuronal cell body be capable of mounting the appropriate biosynthetic response; and the environment surrounding the injury site be capable of supporting the elongation and eventual functional reconnection of the axon. Medium conditioned by nerve cells such as astrocytes and glial cells contains the neuronotropic growth factors and extracellular matrix proteins necessary for nerve regeneration in brain and spinal cord injuries.

Similarly, the treatment of skin, bones, liver, pancreas, cartilage, and other specialized tissues may be treated with media conditioned by their respective specialized cell types, resulting in a conditioned medium containing characteristic extracellular proteins and other metabolites of that tissue type useful for treating wounds to that respective tissue type.

The conditioned cell medium may also be added to devices used in periodontal surgery in order to promote uniform tissue repair, to provide biodegradable contact lenses, corneal shields or bone grafts, to provide surgical space fillers, to promote soft tissue augmentation, particularly in the skin for the purpose of reducing skin wrinkles, and as urinary sphincter augmentation, for the purpose of controlling incontinence.

In another embodiment, the compositions may be lyophilized/freeze-dried and added as a wound filler (e.g., fill holes left from hair plugs for implantation) or added to existing wound filling compositions to accelerate wound healing. In another embodiment, the medium is conditioned with genetically engineered cells to increase the concentration of wound healing proteins in the medium. For example, the cells may be engineered to express gene products such as any of the growth factors listed above.

In yet another embodiment, the growth factor/exosome-enriched conditioned medium may be formulated in a topical treatment for the stimulation of hair growth on the head and eyelashes. For example, the medium may be conditioned using human hair papilla cells. Hair papilla cells are a type of mesenchymal stem cell that plays a pivotal role in hair formation, growth and restoration (Matsuzaki et al., Wound Repair Regen, 6:524-530 (1998)). The conditioned medium is preferably concentrated and applied as a topical formulation. The conditioned media compositions may be formulated for topical applications using an agent(s) that facilitates penetration of the compound into the skin, for example, DMSO, or other lipophilic carriers, including use of liposomes, and applied as a topical application for stimulating hair growth. Alternatively or in addition, ultrasound may be used to enhance penetration and permeation of the conditioned medium components through the stratum corneum. The compositions are expected to promote or restore hair growth when applied topically by providing growth factors and other factors that increase epithelial cell migration to hair follicles. In addition to the growth factors found in the conditioned media, other active agents, such as minoxidil can be used.

In the pathogenesis of hair loss, there is a reduction in blood supply during catagen (the transitional phase of the hair follicle between growth and resting phases) and telogen (the resting phase). Biologically active molecules derived from the conditioned cell medium can be determined and optimized for use during these phases using assays known in the art including the stump-tailed macaque model for male-patterned baldness, see for example, Brigham, P. a., A. Cappas, and H. Uno, The Stumptailed Macaque as a Model for Androgenetic Alopecia Effect; of Topical Minoxidil Analyzed by Use of the Folliculogram, Clin Dermatol, 1988, 6(4): p. 177-87; Diani, A. R. and C. J. Mills, Immunocytochemical Localization of Androgen Receptors in the Scalp of the Stumptail Macaque Monley, a Model of Androgenetic Alopecia, J. Invest Dermatol, 1994, 102(4): p. 511-4; Holland, J. M., Animal Models of Alopecia, Clin Dermatol, 1988, 6(4): p. 159-162; Pan, H. J., et al., Evaluation of RU58841 as an Anti-Androgen in Prostate PC3 Cells and a Topical Anti-Alopecia Agent in the Bald Scalp of Stumptailed Macaques, Endocrine, 1998, 9(1): p. 39-43; Rittmaster, R. S., et al., The Effects of N,N-diethyl-4-methyl-3-oxo-4-aza-5 alpha-androstane-17 beta-carboxamide, a 5 alpha-reductase Inhibitor and Antiandrogen, on the Development of Baldness in the Stumptail Macaque, J. Clin Endocrinol Metab, 1987, 65(1): p. 188-93 (each of which is incorporated by reference in its entirety). Additional models include measuring differences in hair follicle proliferation from follicles cultured from bald and hairy areas, a newborn rat model as well as a rat model of alopecia areata, see, Neste, D. V., The Growth of Human hair in Nude Mice, Dermatol Clin., 1996, 14(4): p. 609-17; McElwee, K. J., E. M. Spiers, and R. F. Oliver, In Vivo Depletion of CD8+T Cells Restores Hair Growth in the DEBR Model for Alopecia Areata, Br J Dermatol, 1996, 135(2): p. 211-7; Hussein, A. M., Protection Against Cytosine Arabinowide-Induced Alopecia by Minoxidil in a Rat Animal Model, Int J Dermatol, 1995, 34(7): p. 470-3; Oliver, R. F., et al., The DEBR Rat Model for Alopecia Areata, J Invest Dermatol, 1991, 96(5): p. 978; Michie, H. J., et al, Immunobiological Studies on the Alopecic (DEBER) Rat, Br J Dermatol, 1990, 123(5): p. 557-67 (each of which is incorporated by reference in its entirety).

In embodiments, eyelash hair may be grown using the skin cream formulation as disclosed herein in the absence of prostaglandins, phosphates, lead, and the like, without changes in eye color or tinting of eyelids.

Other Active Agents

Also, products which may be added include, but are not limited to, antibiotics, antivirals, antifungals, steroids, analgesics, antitumor drugs, investigational drugs or any compounds which would result in a complimentary or synergistic combination with the factors in the conditioned media.

Pharmacologic agents may also be incorporated into preferred embodiments of the conditioned medium formulations, including for example, the addition of vitamins or minerals. For instance, those that function directly or indirectly through interactions or mechanisms involving amino acids, nucleic acids (DNA, RNA), proteins or peptides (e.g., RGD peptides), carbohydrate moieties, polysaccharides, exosomes, liposomes, or other cellular components or organelles for instance receptors and ligands.

The following agents are believed to exert their actions extracellularly or at specific membrane receptor sites. These include corticoids and other ion channel blockers, growth factors, antibodies, receptor blockers, fusion toxins, extracellular matrix proteins, peptides, or other biomolecules (e.g., hormones, lipids, matrix metalloproteinases, and the like), radiation, anti-inflammatory agents including cytokines such as interleukin-1 (IL-1), and tumor necrosis factor alpha (TNF-a), gamma interferon (interferon-y), and Tranilast, which modulate the inflammatory response. Growth factor receptor agonists are also within the scope of possible active agents that may be admixed with the conditioned medium formulations.

Other groups of agents exert their effects at the plasma membrane. These include those involved in the signal transduction cascade, such as coupling proteins, membrane associated and cytoplasmic protein kinases and effectors, tyrosine kinases, growth factor receptors, and adhesion molecules (selectins and integrins).

Some compounds are active within the cytoplasm, including for example, heparin, ribozymes, cytoxins, antisense oligonucleotides, and expression vectors. Other therapeutic approaches are directed at the nucleus. These include gene integration, proto-oncogenes, particularly those important for cell division, nuclear proteins, cell cycle genes, and transcription factors.

Specific growth factors, interleukins and interferons that may be used in accordance with embodiments of the present invention include, but are not limited to:

Epidermal Growth Factor (EGF): promotes proliferation of mesenchymal, glial and epithelial cells;

Platelet-Derived Growth Factor (PDGF): promotes proliferation of connective tissue, glial and smooth muscle cells; and Fibroblast Growth Factors (FGFs): promotes proliferation of many cells; inhibits some stem cells; induces mesoderm to form in early embryos;

Transforming Growth Factors-β (TGFs-β):
Transforming Growth Factor-a- (TGF-α): may be important for normal wound healing;

Nerve Growth Factor (NGF): promotes neurite outgrowth and neural cell survival;

Erythropoietin (Epo): promotes proliferation and differentiation of erythrocytes;

Insulin-Like Growth Factor-I (IGF-I): promotes proliferation of many cell types; and Insulin-Like Growth Factor-II (IGF-II): promotes proliferation of many cell types primarily of fetal origin.

In some embodiments, the interleukins may be used to boost local immune function and/or modulate inflammatory responses. Some of the interleukins and their primary activity include, but are not limited to, the following:

IL1-α and β: co-stimulation of APCs and T cells, inflammation;

IL-2: proliferation of B cells and activated T cells, NK functions;

IL-3: growth of hematopoietic progenitor cells;

IL-4: B cell proliferation, eosinophil and mast cell growth and function, IgE and class II MHC expression on B cells, inhibition of monokine production;

IL-5: eosinophil growth and function;

IL-6: acute phase response, B cell proliferation, thrombopoiesis, synergistic with M-1 and TNF on T cells;

IL-7: T. and B lymphopoiesis;

IL-8: chemoattractant for neutrophils and T cells;

IL-9: hematopoietic and thymopoietic effects;

IL-10: inhibits cytokine production, promotes B cell proliferation and antibody production, suppresses cellular immunity, mast cell growth;

IL-11: synergisitc hematopoietic and thrombopoietic effects;

IL-12: proliferation of NK cells, INF-γ production, promotes cell-mediated immune functions; and IL-13: IL-4-like activities.

In some embodiments, the interferons may be used to boost local immune function and/or modulate inflammatory responses. Some of the interferons and their primary activity include, but are not limited to, the following:

INF-α and -β: antiviral effects, induction of class I MHC on all somatic cells, activation of NK cells and macrophages;

INF-γ: induces of class I MHC on all somatic cells, induces class II MHC on APCs and somatic cells, activates macrophages, neutrophils, NK cells, promotes cell-mediated immunity, antiviral effects;

Tumor Necrosis Factor-α (TNF-α): induces the expression of other autocrine growth factors, increases cellular responsiveness to growth factors and induces signaling pathways that lead to proliferation;

Tumor Necrosis Factor-β (TNF-β): (also called lymphotoxin) ability to kill a number of different cell types, as well as the ability to induce terminal differentiation in others. One significant non-proliferative response to TNF-β is an inhibition of lipoprotein lipase present on the surface of vascular endothelial cells;

Colony Stimulating Factors (CSFs): stimulate the proliferation of specific pluripotent stem cells of the bone marrow in adults. Granulocyte-, Macrophage-CSFs. Epo and IL-3 are also considered a CSF.

One of the newest peptides to be marketed as a treatment for aging skin is the procollagen fragment Lys-Thr-Thr-Lys-Ser (SEQ ID NO:1), also called KTTKS (SEQ ID NO:1). Studies conducted at the University of Tennessee and sponsored by the National Institutes of Health confirmed that this pentapeptide can promote the synthesis of collagen types I and III and fibronectin by cultured fibroblasts (J. Biol. Chem. 268[14]:9941-44, 1993). To enhance penetration of this hydrophilic peptide, palmitoyl—a 16-carbon fatty acid moiety—was added.

Currently, several products containing Pal-KTTKS (SEQ ID NO:2), including REGENERIST, STRIVECTIN-SD, and STRIXADERM-MD, are patented, manufactured, and sold for commercial use.

Pal-KTTKS (SEQ ID NO:2), known commercially as MATRIXYL, has been shown to penetrate human skin and remains in the dermis; according to unpublished reports.

In a double-blind, vehicle-controlled study of 49 women sponsored by Sederma and presented in a poster at the 2002 World Congress of Dermatology in Paris, Pal-KTTKS (SEQ ID NO:2) (3 ppm) decreased skin roughness by 13%, reduced wrinkle volume by 36%, and decreased wrinkle depth by 27% after 4 months of twice-daily application on the face and neck. Skin biopsies performed on six women at 2 and 4 months demonstrated increased density and thickness of elastin fibers, while collagen type IV was improved at the dermal-epidermal junction.

Clinical studies sponsored by Procter & Gamble supported the benefits of Pal-KTTKS (SEQ ID NO:2) on photoaging skin.

In a study presented in a poster at the 2003 American Academy of Dermatology annual meeting in San Francisco, 92 women with moderate to severe photodamage participated in a split-face, randomized, double-blind, vehicle-controlled study. Subjects were treated for 12 weeks with twice-daily applications of facial moisturizer containing 3 ppm of Pal-KTTKS (SEQ ID NO:2). Pal-KTTKS (SEQ ID NO:2) significantly improved facial lines and wrinkles as measured by image analysis of digital photos and expert grading, and did not negatively affect the skin barrier as measured by transepidermal water loss.

Additional studies were performed to compare the effects of Pal-KTTKS (SEQ ID NO:2) (3 ppm) to retinol (700 ppm) in the same vehicle. In a study presented at the 2002 World Congress of Dermatology in Paris, 16 women applied Pal-KTTKS (SEQ ID NO:2) to crow's-feet on one side of the face and retinol to the other for 4 months.

At the end of 2 months, Pal-KTTKS (SEQ ID NO:2) provided greater benefit than did retinol; at 4 months, both agents performed similarly and had reduced wrinkles as much as 50%. The investigators noted that Pal-KTTKS (SEQ ID NO:2) offered these benefits without the irritation that is often associated with retinol use.

Accordingly, in one embodiment of the present invention, a skin cream comprising a combination of growth factor-enriched conditioned medium the use of KTTKS (SEQ ID NO:1) in any form, including Pal-KTTKS (SEQ ID NO:2), together.

Argireline, or acetyl hexapeptide-3, is a synthetic peptide that is touted as a topical alternative to botulinum toxin (BOTOX®) injections.

This peptide was developed and synthesized by Lipotec S. A. in Barcelona, Spain, and is distributed in the United States by Centerchem Inc. Argireline is found in several cosmeceuticals, including AVOTOX, DDF's Wrinkle Relax (HDS Cosmetics Inc.), and INHIBIT (Natuna Bissé). Most products contain 5%-10% argireline; INHIBIT may have the highest concentration at 20%, and costs $135 for 0.5 ounce.

Extensive in vitro studies have been performed to elucidate argireline's mechanism of action (J. Biol. Chem. 272[5]: 2634-39, 1997). One such study demonstrates that the peptide acts by preventing formation of the soluble N-ethylmaleimide-sensitive fusion attachment protein (SNAP) receptor complex, and thus inhibiting vesicle docking. Catecholamine release, including epinephrine and norepinephrine, was inhibited by argireline in vitro. The investigators suggested that this synthetic peptide may have practical medical applications because it mimics the action of clostridial neurotoxins in vitro.

Clinical trials on the efficacy of topically applied argireline are limited. An open-label trial of 5% argireline and an oil-and-water emulsion, applied twice daily, was conducted on 10 women.

Silicone replicas of periorbital rhytides were analyzed using confocal laser scanning microscopy, and demonstrated a 17% improvement after 15 days of treatment and a 27% improvement after 30 days of treatment.

Although argireline clearly demonstrates interesting in vitro activity, larger, more objective clinical studies are necessary to confirm its efficacy. Permeability studies performed on human skin would also be necessary, because this peptide would have to penetrate to the muscles to exert its proposed mechanism of action.

Therapeutic Formulations

The conditioned medium may be formulated for preventing, reducing and/or eliminating wrinkles, frown lines, scarring and other skin conditions associated with aging, in addition to or in the alternative to using surgery, injectables, silicone or other products. Aging skin is characterized by a decrease in collagen synthesis and an increase in collagen breakdown. Some growth factors stimulate collagen production. The conditioned medium contains growth factors and inflammatory mediators such as, for example, PDGF, IGFs, FGFs, TGFs, EGF, VEGF, HGF, IL-6, G-SCF and KGF as well as extracellular matrix proteins such as type I and type III collagens, fibronectin, terascin, glycosaminoglycans, versican, decorin and various other secreted human dermal matrix proteins, which may be useful in repairing physical anomalies and cosmetic defects. In addition to the conditioned medium, peptides such as KTTKS (SEQ ID NO:1) and Pal-KTTKS (SEQ ID NO:2), which promote collagen synthesis, and argireline, a synthetic peptide that inhibits muscle-induced wrinkling of the skin, may also be included as other active agents in the topical formulation.

In one embodiment, the conditioned cell medium is formulated as a cosmeceutical facial cream, lotion, and/or serum for topical application, with or without additional growth factors, exosomes, peptides, and/or other proteins and biologically active substances, including, but not limited to, those discussed herein.

In addition to the other active agents discussed above, typical skin cream formulations may include one of more of the following general types of ingredients:

Emollients, in the form of plant oils, mineral oils, shea butter, cocoa butter, petrolatum, cholesterol, silicones or animal oils (including emu, mink and lanolin). These lubricating ingredients soften and smooth skin while helping it to retain moisture. In some embodiments, jojoba, squalene and lanolin represent recited emollients because they bear the greatest similarity to sebum (the skin's natural moisturizing agent), are the least comedogenic (pore-clogging), and are most compatible with the skin's biochemistry. Thickening agents like triglycerides, palmitates, myristates and stearates are waxier, but necessary for the fundamental base and texture of a moisturizing formulation.

Water-binding agents are ingredients that keep water in the skin. Humectants (including sorbitol, glycols, glycerins and sodium PCA), which attract water to skin, may be desirable in formulations designed to treat/prevent skin damaged by sun and dehydration, but they are less useful in promoting water retention by the skin.

Soothing agents and anti-irritants, such as bisabolol, allantoin, burdock root, aloe, licorice root, glycyrrhetinic acid, green tea and chamomile extract, may be added to help skin handle ingredients that may cause irritation.

Vitamins and antioxidants, including vitamins A, C and E, may be used to promote cell turnover, healing and dehydration.

Alpha hydroxy acids (AHAs) and beta hydroxy acids (BHAs) have been shown to clear pores and remove dead skin, resulting in smoother, moister skin. AHA formulations include glycolic acid and lactic acid, while the use fruit or citrus acid, sugarcane, or even sour milk may be substituted. One BHA ingredient is salicylic acid. However, high levels of AHAs may feel tingly on certain skin types. Also, because AHA increases sun sensitivity, sun protection (e.g., addition of physical and/or chemical sunscreen agents) may be desirable for formulations which incorporate an AHA.

In one embodiment, the formulated skin cream combines therapeutically effective amounts of conditioned medium (or concentrates or extracts thereof) with a thickener, a humectant, allantoin, purified water, and at least one preservative.

In another embodiment, the thickener comprises a combination of polyethylene glycol (PEG), a vegetable-based fatty alcohol(s), and a copolymer(s).

Some preferred vegetable-based fatty alcohols include, but are not limited to: decyl alcohol, octyl-decyl alcohol, lauryl alcohol, lauryl-myristyl alcohol, myristyl alcohol, cetostearyl alcohol and its various blends, cetyl alcohol, and stearyl alcohol.

Copolymers may include those conventionally used in cosmeceuticals, as known by those skilled in the art.

In another embodiment, the thickener comprises PEG-150, decyl alcohol, and SMDI copolymer.

Some humectants include, but are not limited to: sodium PCA, glycerine, propylene glycol, sorbitol, hyaluronic acid, urea, and lactic acid.

Some preservatives include, but are not limited to: heterocyclic compounds, methylparaben, propylparaben, diazolidinyl urea, phenoxyethanol, DMDM hydantoin, sorbic acid, benzyl alcohol, formaldehyde, triclosan and EDTA.

Some heterocyclic compounds include, but are not limited to: methylisothiazolinone, methylchloroisothiazolinone, and caffeine.

In one embodiment, the formulated cream combines the conditioned medium (or concentrates or extracts thereof) with PEG-150/decyl alcohol/SMDI copolymer, sodium PCA, allantoin, purified water, methylisothiazolinone, and methylparaben.

In other embodiments, the conditioned media may be formulated into pharmaceuticals in the form of skin patches, injectables, hydrogels and into any other appropriate formulation known to one of skill in the art.

The pharmaceutical/cosmeceutical formulations may be delivered to a subject via a variety of routes using standard procedures well known to those of skill in the art. For example, such delivery may be site-specific or general topical administration, including the use of transdermal stamps. Also, they may be formulated to function as controlled, slow release vehicles. In addition, specifically designed disposable applicators may also be used (e.g., for eyelash rejuvenation/growth).

Therapeutic products contained in the conditioned media include, but are not limited to, nucleic acids, peptides, growth factors, enzymes, hormones, cytokines, antigens, antibodies, clotting factors, and regulatory proteins. Therapeutic proteins include, but are not limited to, inflammatory mediators, argiogenic factors, Factor VIII, Factor IX, erythropoietin, alpha-1 antitrypsin, calcitonin, glucocerebrosidase, human growth hormone and derivatives, low density lipoprotein (LDL), Erythropoietin (EPO), and apolipoprotein E, IL-2 receptor and its antagonists, insulin, globin, immunoglobulins, catalytic antibodies, the interleukins, insulin-like growth factors, superoxide dismutase, immune responder modifiers, BMPs (bone morphogenic proteins) parathyroid hormone and interferon, nerve growth factors, tissue plasminogen activators, and colony stimulating factors. Of course, the medium may be further processed to concentrate or reduce one or more factor or component contained within the medium, for example, enrichment of a growth factor using immunoaffinity chromatography or, conversely, removal of a less desirable component, for any given application as described herein.

Assays commonly employed by those of skill in the art may be utilized to test the activity of the particular factor or factors, thereby ensuring that an acceptable level of biological activity (e.g., a therapeutically effective activity) is retained and/or generated by post-harvest processing. Doses of such therapeutic factors are well known to those of skill in the art and may be found in pharmaceutical compedia such as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publ., THE CHEMOTHERAPY SOURCE BOOK, Williams and Wilkens Publishers.

The therapeutically effective doses of any of the growth factors, drugs or other active agents described above may routinely be determined using techniques well known to those of skill in the art. A "therapeutically effective" dose refers to that amount of the compound sufficient to result in amelioration of at least one symptom of the processes and/or diseases being treated.

Toxicity and therapeutic efficacy of the drugs can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, some of the growth factors secreted into the medium have the following concentrations:

TGF Beta-1 at about 0.01-100 ng/mL, about 0.1-10 ng/mL, or about 1-3 ng/mL.

TGF Beta-2 at about 0.1-1000 pg/mL, about 1-1000 pg/mL, or about 100-160 pg/mL.

TGF Beta-3 at about 0.1-1000 pg/mL, about 1-1000 pg/mL, or about 50-100 pg/mL.

IL-3 at about 0.1-1000 pg/mL, about 1-1000 pg/mL, or about 60 pg/mL.

IL-6 at about 0.1-1000 ng/mL, about 1-100 ng/mL, or about 11 ng/mL.

IL-7 at about 0.1-1000 pg/mL, about 1-100 pg/mL, or about ~50 pg/mL.

IL-8 at about 0.1-1000 ng/mL, about 1-100 ng/mL, or about ~4-10 ng/mL.

In embodiments, conditioned media contains about 1.5 to about 10 fold more exosomes compared to non-enriched conditioned media.

In another embodiment, growth factor-enriched conditioned medium from melanocytes and/or other cell types may be combined with conditioned medium from fibroblasts. The concentration of FGF-2 secreted by melanocytes typically ranges from about 10-10,000 pg/mL, about 100-1000 pg/mL, or about 400-450 pg/mL.

In one embodiment, a kit is disclosed including a skin cream comprising a conditioned medium or extract or concentrate thereof, from cultured substantially homogenous foreskin derived fibroblast cells, where the conditioned medium is generated by incubating a nutrient medium with the cells in two-dimensional culture under conditions adapted to promote secretion of at least one growth factor into the nutrient medium, and where the at least one growth factor is present in the conditioned medium or extract or concentrate thereof in an amount sufficient to treat or prevent the skin defect; a container; a label; and instructions which provide methods of applying the skin cream. The instructions may be a pamphlet, CD, or other computer readable medium. Further, the instructions may provide information about a website which may contain downloadable content.

The following examples are intended to illustrate but not limit the invention.

EXAMPLES

1. Isolation of Human Foreskin Fibroblasts
   I. Materials
   100 mm sterile tissue culture dishes
   150 mm sterile tissue culture dishes
   Sterile scalpel blades
   Sterile full-curved forceps
   Sterile half-curved scissors
   50 ml Centrifuge Tubes
   1, 5, and 10 ml Pipette Tips
   Pipettes
   Dulbecco's Modified Eagle's Medium (DME/High Modified)
   Fetal Bovine Serum (FBS)
   Antibiotic-Antimycotic (ABAM)
   L-Glutamine (L-GLU)
   Phosphate Buffer Saline (PBS)
   Trypsin-EDTA 1× (0.25% Trypsin 1 mM EDTA-4Na. Prepared with 2.5 g Trypsin (250) and 0.38 g EDTA-4Na in 1 liter of HBSS without Ca and Mg++.
   Transport Media:
   ADD to 500 ml bottle of DMEM:
   FBS 50 ml
   ABAM 5 ml
   Growth Media (GM):
   ADD to 500 ml bottle of DMEM: Final Conc.
   FBS 50 ml 10%
   ABAM 5 ml 1%
   L-glu 5 ml 292 ng/ml.
   II. Isolation Technique Foreskins were obtained from newborn babies after circumcision and were donated by their parents. Samples were transported in a sterile centrifuge tube with 5 ml Transport Media at room temperature. The samples were removed from the tube with a sterile pipette and placed in a 100 mm tissue culture dish. The cells were washed three times with PBS-CMF/1% ABAM. Subcutaneous fatty tissue was trimmed with curved scissors and forceps.

The samples were split horizontally into 0.5×1.0 cm$^2$ pieces and placed in a 100 mm tissue culture dish with the epidermis side down. Ten ml of Trypsin-EDTA 0.25% and refrigerate (4° C.) overnight (16-18 hrs) was then added.

Samples are taken from the refrigerator and epidermis was separated from dermis using two forceps. Under these conditions the epidermis should peel off easily from dermis. Trypsin exposed single cells were removed and placed in centrifuge tube and 15 ml of GM was added to stop the action of Trypsin. The resulting solution was then centrifuged for 10 minutes at 800×g in a Sorvall Highconic fixed angle rotor.

Fibroblasts were isolated by taking the dermis explants and mincing them into fine pieces, where they were plated on 100 mm petri dishes. The foreskins were washed, minced by scissors, and dissociated to single cells by trypsinization. The resulting cells were grown in a culture medium consisting of 80% Dulbecco's modified Eagle medium (DMEM; no pyruvate, high-glucose formulation) supplemented with either 20% fetal bovine serum (FBS; Hyclone, Logan, Utah); 20% SR; or 20% human serum (Chemicon International, Temecula, Calif.), 2 mM L-glutamine, 0.1 mM β-mercaptoethanol, and 1% nonessential amino acid stock (Gibco Invitrogen Corporation, Carlsbad, Calif.). The foreskin cells were split using trypsin-EDTA (0.5% trypsin and 0.25% EDTA; Gibco Invitrogen) every 5-7 days. Ten ml of fibroblasts media was added to the cells, which were then placed in incubator without disturbance for 48 hours. The cells were passaged and expanded once, where the dishes were at about 50-60% confluent. For immortalized cells, expanded cultures were transfected with pBsSVD2005 according to the manufacturer's instructions (i.e., Addgene, Inc., Cambridge, Mass.).

Trypsinizing was accomplished by removing the spent media. Five ml of Trypsin 0.25% was added and cells were incubated at 37° C./5% $CO_2$ for 10 minutes. The culture was checked frequently under the microscope to ensure that cells were peeling off Where necessary, the dishes were tapped on the side to help dislodge cells.

When cell-peeling was confirmed, 5 ml of GM was added to stop the action of Trypsin. Single cells were place in a centrifuge tube and centrifuged for eight minutes at 800×g in a Sorvall Highconic fixed angle rotor. The supernatant was removed and resulting cells were resuspended DMEM with 5%-20% FBS.

2. Method of Cell Culture

This protocol is for use of the wave bioreactor with Nunc MicroHex microcarriers (Nalge Nunc International, Denmark). Nunc MicroHex are 2D, flat hexagonal shaped polystyrene carriers with side lengths of 125 microns.

I. Inoculation

The Cellbag (Wave Biotech) was inflated with air and 10% $CO_2$ until rigid. Media was added and the inlet and outlet filters were clamped. The Cellbag were then rocked at about 15 rocks per minute (rpm) and an angle of about 7 degrees. The temperature and pH were allowed to equilibrate. The initial volume was about 50% of the final culture volume. The microcarriers and cell suspension were then added. Generally, an initial cell density of about 0.1-0.5×10$^6$ cells per mL was added. The inlet and outlet filters were kept clamped and rocking was continued at a rate of about 20 rpm and an angle of about 7 degrees. The attachment process was continued over several hours or overnight.

II. Operation

Once the cells were attached, the remaining amount of media was added to bring the culture up to final volume. Cell density, viability, and metabolism were monitored while the cells were growing. The oxygen levels were monitored and the rpm and angle adjusted in response to oxygen demands of the culture. It is best to maintain a low rpm and angle while maintaining sufficient oxygen and keeping the microcarriers/cells suspended. As the cells continued to grow the media eventually became spent. Media exchange was accomplished by shutting off the rocking. With the platform tipped forward, the microcarrier/cell complexes settled to the bottom edge of the Cellbag within minutes. The media was then be pumped out without removing any of the microcarriers. Up to 90% of the culture volume was removed in this manner. Fresh prewarmed media was added and rocking the Cellbag was resumed at the previous settings.

III. Rocking Speed

The rocking speed was dependent on the culture volume, cell density, and Cellbag size cell or culture flask or petri dish.

For Cellbag 2 L and 10 L, the speed was set at about 15 to 20 rpm initially. The speed was increased to about 20 to 25 rpm as the cell density increased.

IV. Rocking Angle

For Cellbag 2 L and 10 L, an initial angle of 6 degrees was sufficient. When max cell density was achieved, an angle of about 7-8 degrees was preferred.

V. Aeration Rate

The Cellbag was kept rigidly inflated. During Cellbag inflation, a flow rate of up to about 0.5 L per minute (1 pm) was used. Once vigorous growth was observed, the flow rate was set to about 0.1 1 pm for the 2 L bag, and about 0.2 1 pm for the 10 L Cellbag.

VI. Operating Temperature

Typical operating temperature for mammalian cells is 36-37 degrees C.

VII. pH Control pH control is extremely critical. Due to the high gas transfer capacity of the Wave bioreactor, pH may drift rapidly. The following procedure was used:

a. the Cellbag was initially inflated with 10% $CO_2$/air. After inflation, media and microcarriers were added to the bioreactor and the inlet and outlet air filters were closed off. For the pH and temperature to completely equilibrate, the Cellbag was allowed to rock 1-2 hours at about 15 rpm. Before inoculation, the pH was checked by taking a sample and adjusted when necessary.

b. The microcarriers were inoculated with cells, where the inlet and outlet filters remained closed.

c. Monitoring pH, glucose concentration and cell density. Once the pH and glucose levels started dropping, continuous airflow through the headspace was switched to 5% $CO_2$/air. This occurred within 24-60 hours. Once vigorous cell growth occurred, the media pH did not drift upwards and $CO_2$ concentration in the sweep gas functioned to control pH.

d. The rock rate and angle were increased to maintain oxygen concentration.

e. Care was taken when replacing spent media. The pH was monitored and $CO_2$ concentration was adjusted as cells became acclimated to the fresh media.

VIII. Scale Up

A typical scale up for a cell line on Nunc microcarriers is given below:

a. 500 mL media was used to fill a 2 L Cellbag. Thirteen grams of MicroHex carriers was added and pH was allowed to equilibrate. Enough cell inoculum was added to give a starting cell count of at least $0.3 \times 10^6$ cells/mL ($1.5 \times 10^8$ cells total). The rock rate was set at about 15 rpm and at an angle of about 6 degrees overnight. The system was kept at operating temperature.

b. The next day 500 mL of media was added, and the rpm was adjusted to about 18, while the angle was adjusted to about 6 degrees.

c. Culturing was continued for another day until the pH began to drop. The inlet and outlet filters were unclamped and continuous air/$CO_2$ flow was commenced. The oxygen levels in the culture carefully were monitored carefully. The rpm was adjusted to about 20.

d. Culturing was continued for a few more days until glucose levels and low pH indicated that the media was spent. Fifty percent of the media was exchanged, with careful monitoring of the pH. The rpm was adjusted to about 22 and the angle was adjusted to about 7 degrees.

e. The 50% media change was continued every second day.

When the cells reached about 80-95% confluence, the conditioned media was then used for exosome isolation.

Exosome Isolation

The conditioned media was centrifuged at 12,000×g for about 15 min. at about 4° C. (low speed centrifugation). The resulting supernatant was then centrifuged at 100,000×g for about 1 hr at about 4° C. The resulting pellet was then re-suspended in 4° C. phosphate buffered saline, and the re-suspended material was then re-centrifuged for 1 hr at 100,000×g, 4° C.

This resulted in about 1-4 µg exosomes/ml culture from the media, as determined by ELISA or FACS.

When sufficient exosomes were isolated to achieve at least about a 20% increase above the exosome population in the non-enriched culture was obtained, they were resuspended in conditioned media (about 1-5 ml), and added to the various compositions as set forth below.

Formulations

AQ Skin Solution Active Serum

| Ingredient* | Function | Wt % |
|---|---|---|
| Water (Aqua) | Base solvent | 65.00 |
| Conditioned Media w/ or w/o exosomes | Skin-conditioning agent | 24.24 |
| Glycerin | Humectant | 4.00 |
| Polysorbate 20 | Oil solubilzer | 2.50 |
| Cellulose Gum | Thickener | 1.50 |
| Tetrahexyldecyl Ascorbate | Antioxidant | 0.50 |
| Tocopheryl Acetate | Antioxidant | 0.50 |
| Lactic Acid | pH adjuster | 0.16 |
| Citrus Aurantium Berganmia (Bergamot) Fruit Oil | Skin-conditioning agent | 0.10 |
| Phenoxyethanol | Preservative | 0.60 |
| 1,2-Hexanediol | Solvent | 0.45 |
| Caprylyl Glycol | Emollient | 0.45 |

*Standard: ICID

AQ Skin Solution Eye Serum

| Ingredient* | Function | Wt % |
|---|---|---|
| Water | Base, Solvent | 46.95 |
| Conditioned Media w/ or w/o exosomes | Skin Conditioning | 30.00 |
| Acetyl Hexapeptide-3 | Lifting, Anti-Wrinkle | 4.00 |
| Glycerin | Humectant | 6.95 |
| Hesperidin Methylchalcone | Anti-Puffiness | 0.30 |
| Steareth-20 | Dispersant | 0.30 |
| Dipeptide-2 | Anti-Puffiness | 0.10 |
| Palmitoyl Tetrapeptide 7 | New Generation Peptides | 0.30 |
| Butylene Glycol | Humectant | 2.00 |
| Orenothera Biennis (Evening Primrose) Seed Extract | Botanical | 1.00 |
| Polysorbate 20 | Oil Solubilizer | 2.50 |
| Chrysin | Antioxidant | 0.10 |
| N-Hydroxysuccinimide | Lessens Dark Circles Under Eye | 0.10 |
| Palmitoyl Oligopeptide | New Generation Peptides | 0.10 |
| Aminoethylphosphinic Acid | Humanctant | 1.50 |
| Xanthan Gum | Thickener | 0.90 |
| Green Tea Extract (Camellia Sinesis) | Botanical | 0.50 |
| Citrus Gandis (Grapefruit) Extract | Botanical | 0.25 |
| Lactic Acid | pH Adjuster | 0.15 |
| Citrus Aurantium Bergamia (Bergamot) Fruite Oil | Skin-Conditioning agent | 0.10 |
| Phenoxyethanol | Preservative | 0.60 |
| 1,2-Hexanediol | Antimicrobial | 0.65 |
| Caprylyl Glycol | Emollient | 0.65 |

*Standard: ICID

AQ Skin Solution Hair Complex

| Ingredient* | Function | Wt % |
|---|---|---|
| Water (Aqua) | Base | 30.00 |
| Conditioned Media w/ or w/o exosomes | Skin-Conditioning | 40.00 |
| Propylene Glycol | Solvent | 29.00 |
| *Lonicera Caprifolium* (Honeysuckle) Flower Extract | Botanical | 0.10 |
| *Lonicera Japonica* (Honeysuckle) Flower Extract | Botanical | 0.10 |
| 1,2-Hexanediol | Solvent | 0.40 |
| Caprylyl Glycol | Emollient | 0.40 |

*Standard: ICID

AQ Vaginal Rejuvenation Serum

| Ingredient* | Function | Wt % |
|---|---|---|
| Water (Aqua) | Base | 28.75 |
| Conditioned Media | Skin-Conditioning | 30.00 |
| Glycerin | Humectant | 20.00 |
| *Simmondsia Chinensis* (Jojoba) Seed Oil | Botanical | 18.00 |
| Xanthan Gum | Thickener | 1.00 |
| Hydroxyethyl Acrylate/Sodium Acryloyldimethyl Taurate Copolymer | Antioxidant | 0.66 |
| Squalane | Emollient | 0.17 |
| Polysorbate 60 | Oil Solubilizer | 0.17 |
| *Rosmarinus Officinalis* (Rosemary) Leaf Oil | Botanical | 0.80 |
| Lactic Acid | pH Adjuster | 0.15 |
| Chlorphenesin | Preservative | 0.30 |

AQ Lash

| Ingredient* | Function | Wt % |
|---|---|---|
| Water (Aqua) | Base | 57.00 |
| Conditioned Media | Skin-Conditioning | 40.00 |
| Glycerin | Humectant | 1.497 |
| Panthenol | Preservative | 0.500 |
| Biotinoyl Tripeptide-1 | Active Agent | 0.10 |
| *Lonicera Caprifolium* (Honeysuckle) Flower Extract | Botanical | 0.100 |
| *Lonicera Japonica* (Honeysuckle) Flower Extract | Botanical | 0.100 |
| 1,2-Hexanediol | Solvent | 0.400 |
| Caprylyl Glycol | Emollient | 0.400 |

Example 1

Comparison Study

The skin cream composition (AQ Skin Solution Active Serum, without enriched exosomes) was formulated as above, with the proviso that the skin conditioning agent (i.e., conditioned media) concentration was varied (i.e., at 42%, 30%, and 20%; wt %). The composition was topically administered to the skin of human subjects and a physical evaluation was performed by a staff RN or staff physician.

Subjects

The study was conducted using 20 subjects (13 females, 7 males) between the ages of 25-72 yrs old. Volunteers signed comprehensive informed consent documents.

Standard scoring system was used based on 10 questions, including 94% of women overall appearance of their skin, improvement in skin texture/smoothness, increase in skin firmness and elasticity, and reduction in the appearance of fine lines and wrinkles.

Subjects were given unlabelled containers of the 4 products including a placebo. Period of study—75 days. The AQ product was compared against TNS RECOVERY COMPLEX™ (Skin Medica), BIO-GEL bio-restorative Biogel (Neocutis), and Revive Moisture renewal cream (ReVive). The results of study are shown in FIG. 2 (skin conditioning agent at 42%).

Results

Figure 2:
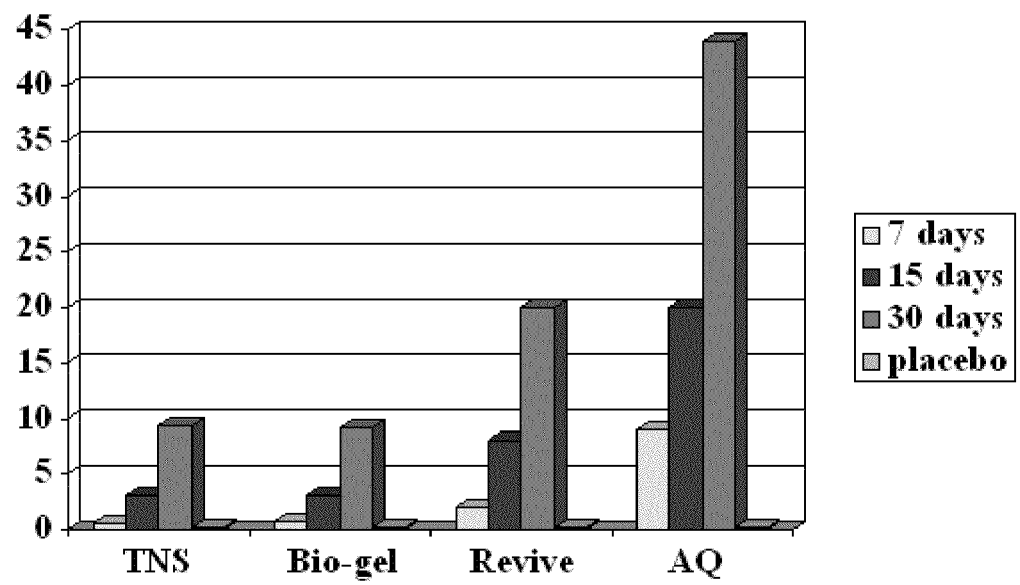
FIG. 2 shows the results of a comparison study conducted using 20 subjects between the ages of 25-72 yrs old. Subjects were given unlabelled containers of the 4 products (AQ Product; TNS, BIO-GEL, and Revive) including a placebo. Period of study—75 days.
Figure 3:
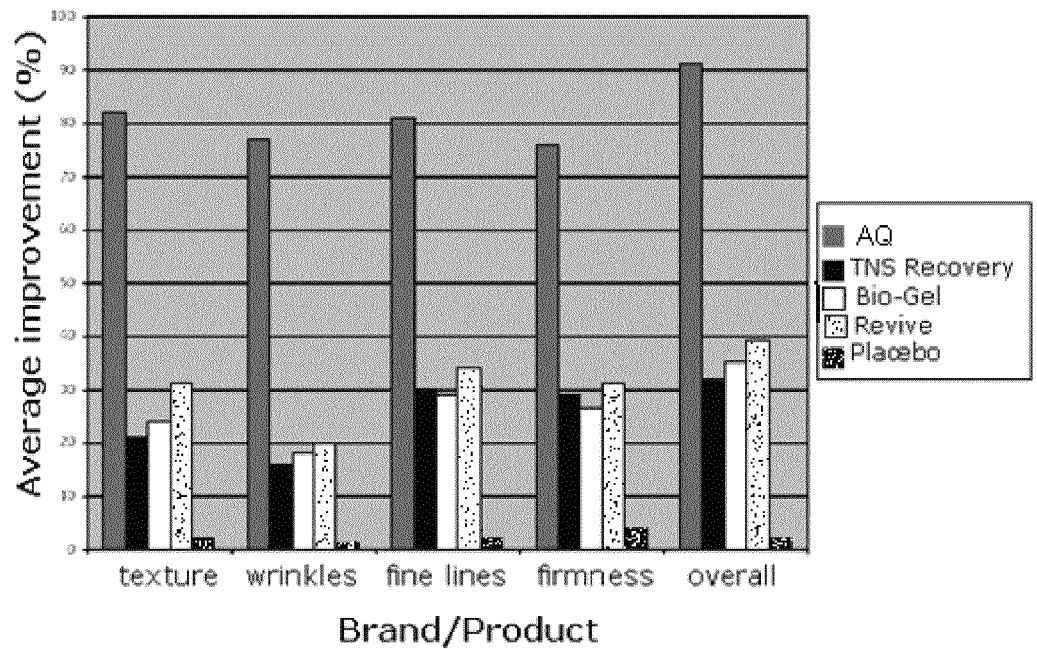
FIG. 3 shows the average percent improvement scores for texture, wrinkles, fine-lines, firmness, and overall improvement of the skin at 42% (wt %).

As demonstrated in FIG. 2, the AQ product was shown to give at least a 2 fold better results at each time point compared to TNS, BIO-GEL and ReVive products. FIG. 3 shows the average percent improvement scores for texture, wrinkles, fine-lines, firmness, and overall improvement of the skin.

Figure 4:
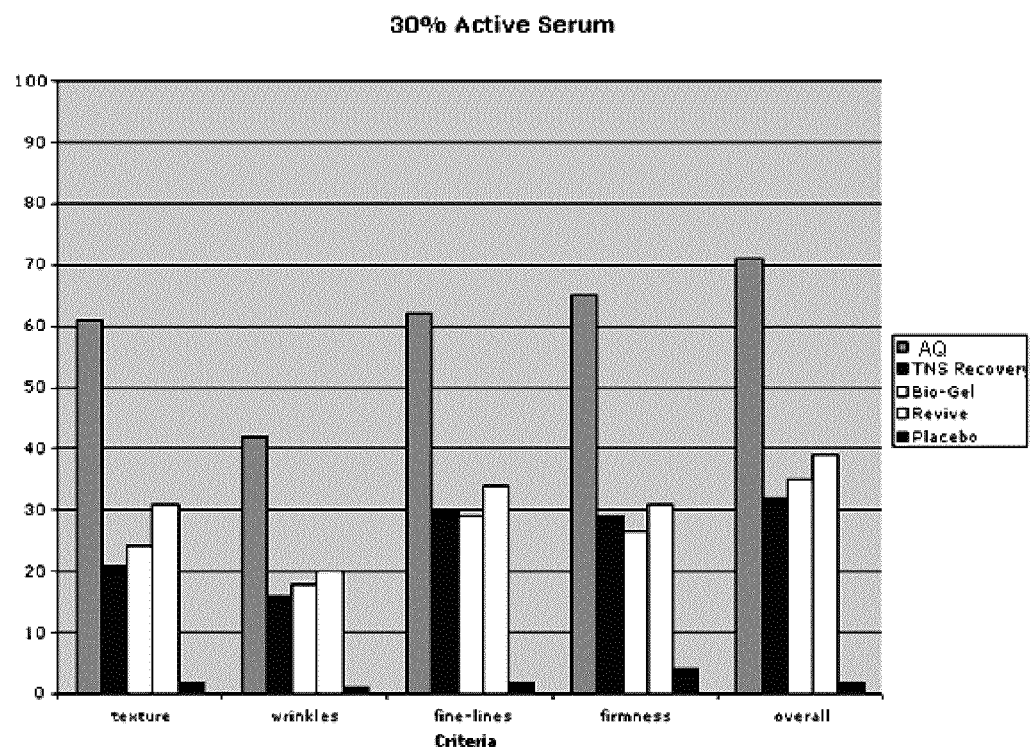
FIG. 4 shows the average percent improvement scores for texture, wrinkles, fine-lines, firmness, and overall improvement of the skin at 30% (wt %).
Figure 5:
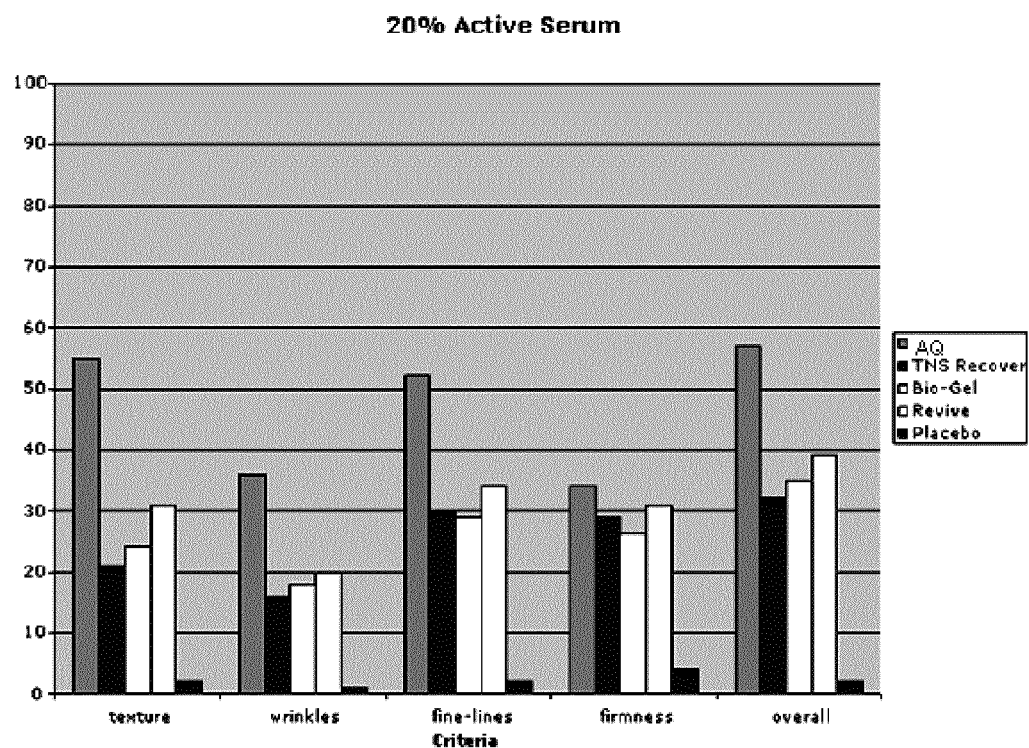
FIG. 5 shows the average percent improvement scores for texture, wrinkles, fine-lines, firmness, and overall improvement of the skin at 20% (wt %).
Figure 6:
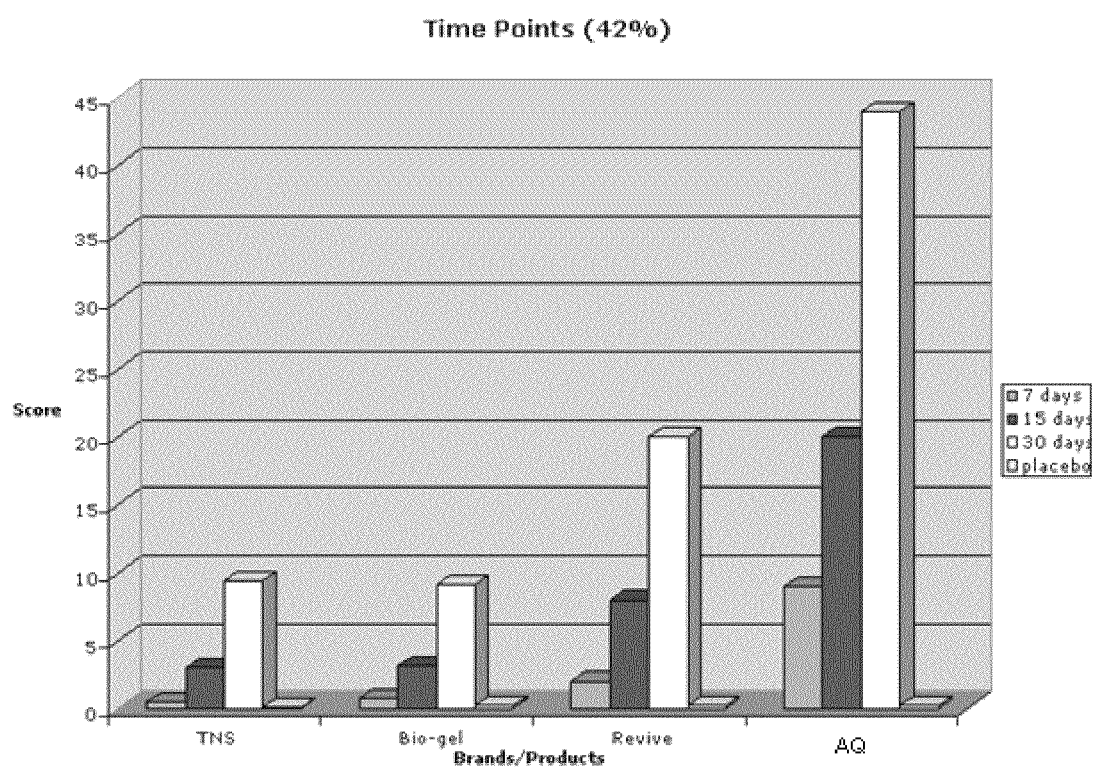
FIG. 6 shows efficacy at various time points for the comparison study. Time points at 7, 15, and 30 days (42%, wt %).
Figure 7:
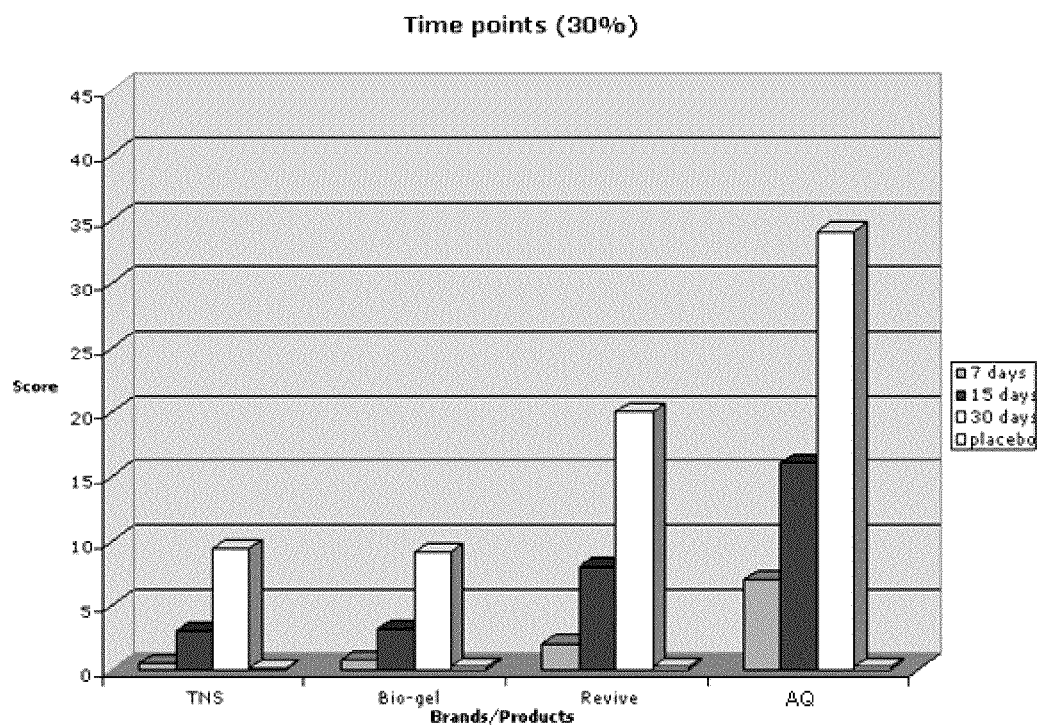
FIG. 7 shows efficacy at various time points for the comparison study. Time points at 7, 15, and 30 days (30%, wt %).
Figure 8:
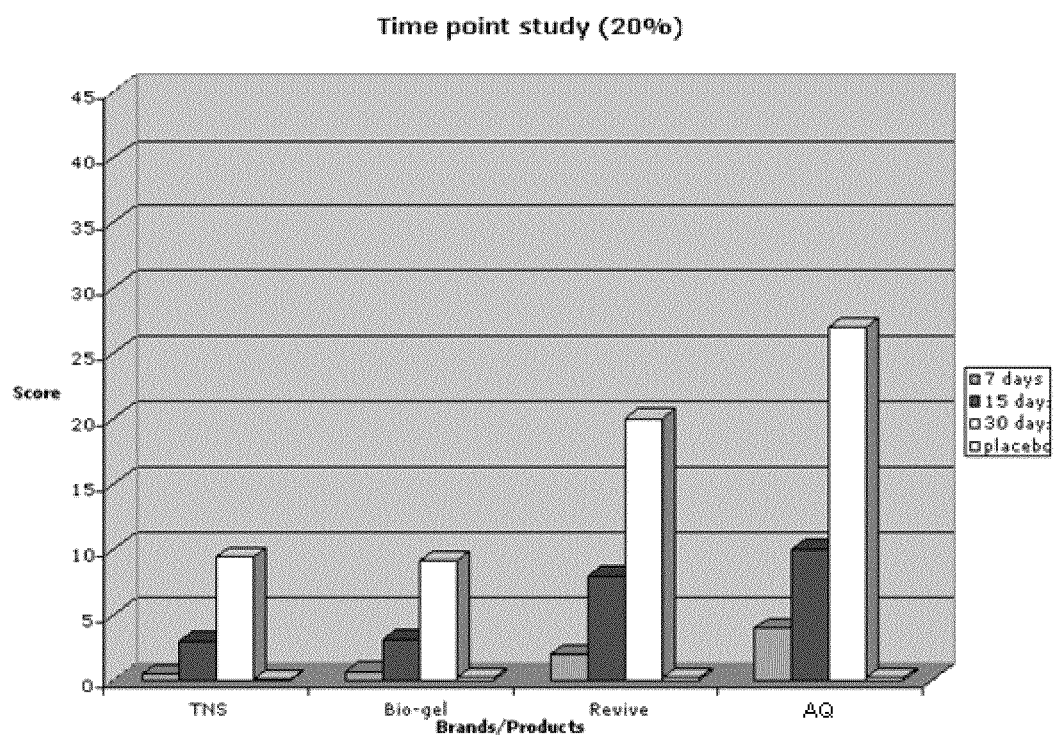
FIG. 8 shows efficacy at various time points for the comparison study. Time points at 7, 15, and 30 days (20%, wt %).

In order to determine the minimal amount of skin conditioning agent necessary for efficacy, AQ products having different concentrations of skin conditioning agents were examined. The results of the examination are show in FIGS. 3-5, including time point analysis (i.e., FIGS. 6-8).

As can be seen from the data, 5% seems to be the minimal concentration necessary for efficacy.

Example 2

Acne Scarring

The skin cream composition (AQ Skin Solution Active Serum) was formulated as above. The composition was topically administered to the skin of human subjects and a physical evaluation was performed by a staff RN or staff physician.

Subjects

The study was conducted using 20 subjects (13 females, 7 males) between the ages of 25-72 yrs old. Volunteers signed comprehensive informed consent documents.

Figure 9:
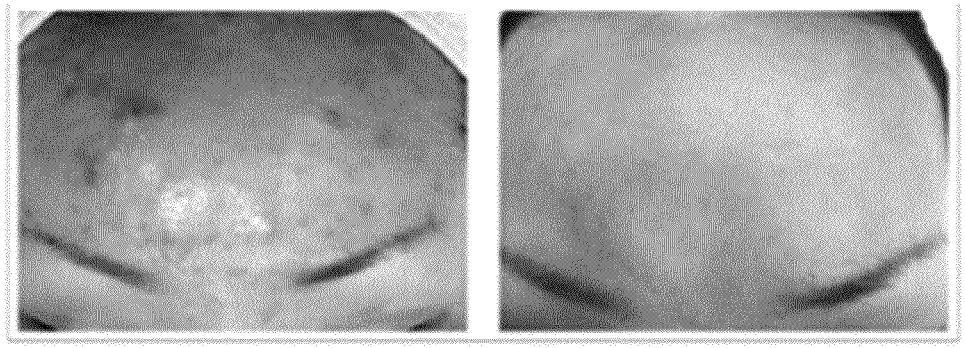
FIG. 9 shows before and after treatment using the AQ Skin Treatment Composition in conjunction with a dermatological transdermal delivery stamp. The subject had acne scars on the forehead.
Figure 10:
FIG. 10 shows before and after treatment using the AQ Skin Treatment Composition in conjunction with a dermatological transdermal delivery stamp. The subject had acne scars on the cheeks.
Figure 10:
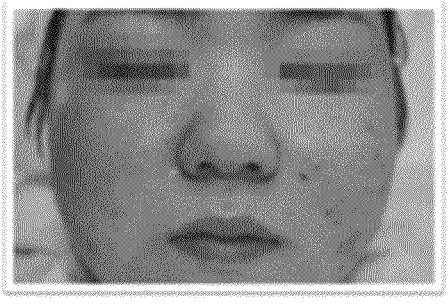

Subjects were given AQ Skin Solution Active serum via administration with a transdermal skin stamp. The results of study are shown in FIGS. 9 and 10.

Results

As demonstrated in the before and after pictures, (i.e., FIGS. 9 and 10), the AQ product reduced or completely removed acne scars from the subjects' skin.

Example 3

Male Pattern Baldness

The goal of this study was to test naturally occurring growth factors, specifically the components of AQ's Active Hair Serum, in the treatment of Androgenetic alopecia (AGA).

Subjects

Included in this study were 72 subjects (males and females) between the ages of 25 and 65 years of age, in good health, with mild to moderate AGA. Volunteers signed comprehensive informed consent documents. Subjects were treated with the AQ Active Hair Serum for 15 weeks.

Results

Efficacy measurements were administered at baseline, and then at a final visit. The measurements were: 1) investigative staff assessed hair growth and 2) patient self-assessment of treatment efficacy and satisfaction with appearance.

Patient Self-Assessment

The parameters assessed by study subjects in this analysis were the following questions: a) size of bald spot; b) appearance of hair; c) growth of hair; d) rate of hair loss; and e) satisfaction with appearance of hair. Other measures included hair thickness, length, strength (tension), hair loss prevention, scalp rejuvenation, and overall growth.

Figure 11:
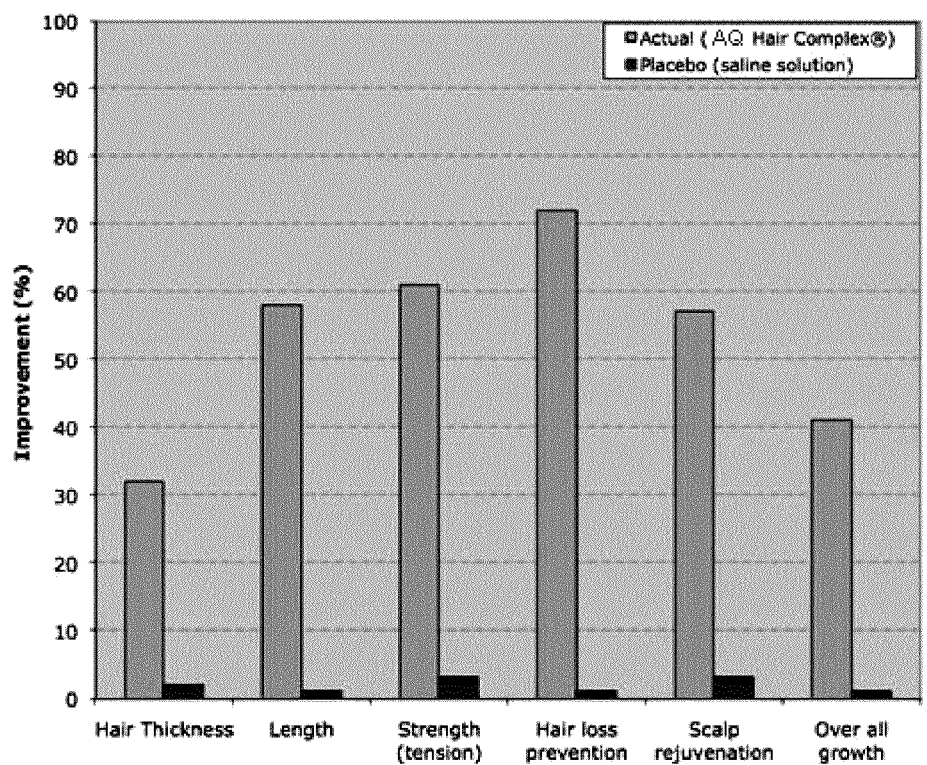
FIG. 11 shows a graph demonstrating improvement in hair growth parameters for 72 subjects using AQ Hair Serum vs. placebo (saline).
Figure 12:
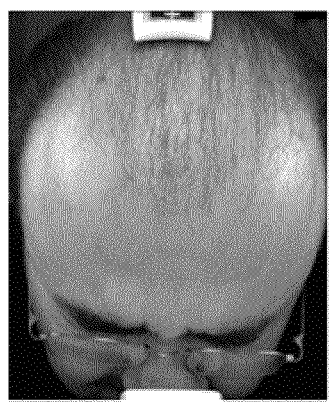
FIG. 12 shows progressive hair growth on the scalp of a subject treated with the AQ composition over a 15 week period. Pictures show results at 0, 8, and 15 weeks.
Figure 12:
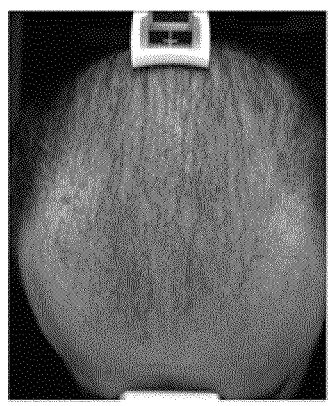
Figure 12:
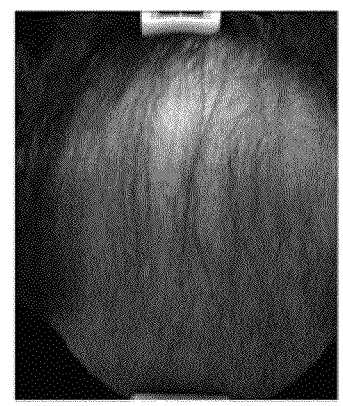
Figure 13:
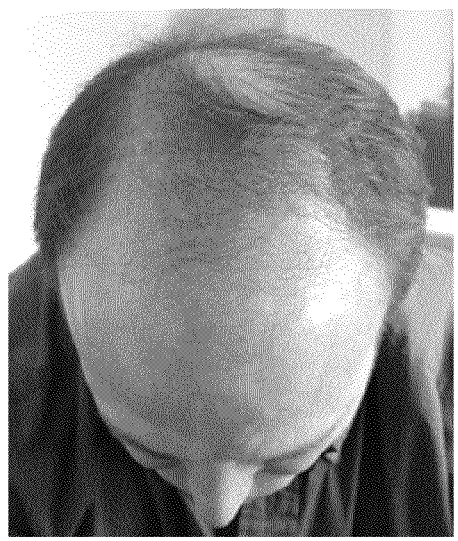
FIG. 13 shows progressive hair growth on the scalp of another subject treated with the AQ product over a 15 week period. Pictures show results at 0 and 15 weeks.
Figure 13:
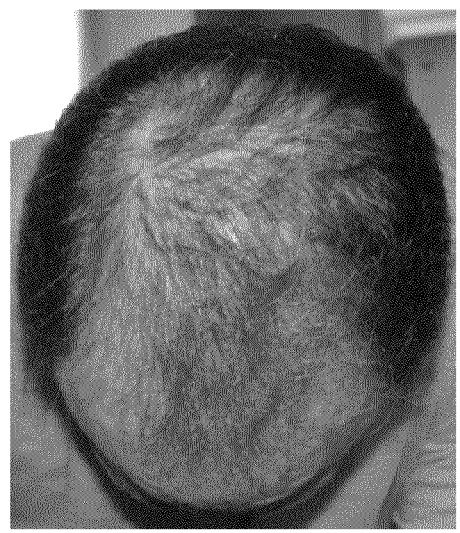

The results of this study showed a highly positive response to treatment (see FIGS. 11, 12 and 13). The blinded investigative staff assessment report showed that over 90% of study subjects dosed with the active study formulation were rated as improved at the final visit.

Conclusions

This study establishes the effectiveness of naturally occurring growth factors in the treatment of hair loss, and demonstrates that the Hair Serum generates completely new hair follicles in normal adult mammals.

The researchers were able to induce the regenerative response, including new hair follicle formation, by applying a combination of factors to the scalp. The work demonstrated that the induction of this primitive state in skin triggered corresponding embryonic molecular pathways distinct from those active in corresponding cells in adult skin, allowing a new topical treatment option for regrowing hair not previously thought to have therapeutic benefit in normal adult skin.

Example 4

Skin Rejuvenation and Wrinkle Diminishment

Subjects Chosen for the study

Eighty-one (81) males and females between 30 to 78 years of age of good general health not nursing or pregnant with demonstrable fine or deep wrinkles in the face, including around both eyes, at least barely visible dark areas, and at least slightly coarse and grainy lower eyelids. Volunteers signed comprehensive informed consent documents.

Subjects that were not Included

Subjects with any active or any history of skin disease affecting the face area or under the eyes were not included. In addition, subjects were asked to stop their current regime of using any products that may enhance skin condition and aid in reduction of wrinkles. Make-up and sunscreens were permitted. Subjects, who have undergone cosmetic surgery affecting facial skin within 6 months, were also excluded from the study.

Treatment Regimen

AQ Active Serum was applied in mornings and evenings to the facial skin, including the peri-orbital skin area over a period of six weeks (42 days). Subjects were asked to document each application of AQ Active Serum.

Evaluation at baseline and after 6 weeks

Subjects were evaluated by:

1—Clinical assessment:

Clinical photography under standardized conditions.

VISIA-CR imaging (Canfield Scientific, Inc., Fairfield, N.J.).

Clinical assessment of skin quality, including the peri-orbital skin using 1- to 10-point visual scoring system given in Table 1.

2—Self-assessment:

Quality of facial skin, including the peri-orbital skin by subject using questionnaire given.

Results

Of the 81 subjects enrolled, 79 subjects averaged 52±9 years of age (between 30 to 78 years) completed the study. Two subjects dropped out of the study for product unrelated reasons. Results were tabulated using scores generated by the clinical evaluations (Table 1) and subject questionnaire.

TABLE 1

Clinical Scores for Quality of Skin.

| Clinical evaluaion | Scores |
| --- | --- |
| Texture | 1-10 |
| Wrinkles | 1-10 |
| Fine-lines | 1-10 |
| firmness | 1-10 |

1 = no improvement (lowest possible score)
2-9 = different degrees of improvement
10 = great improvement (highest possible score)

Figure 14:
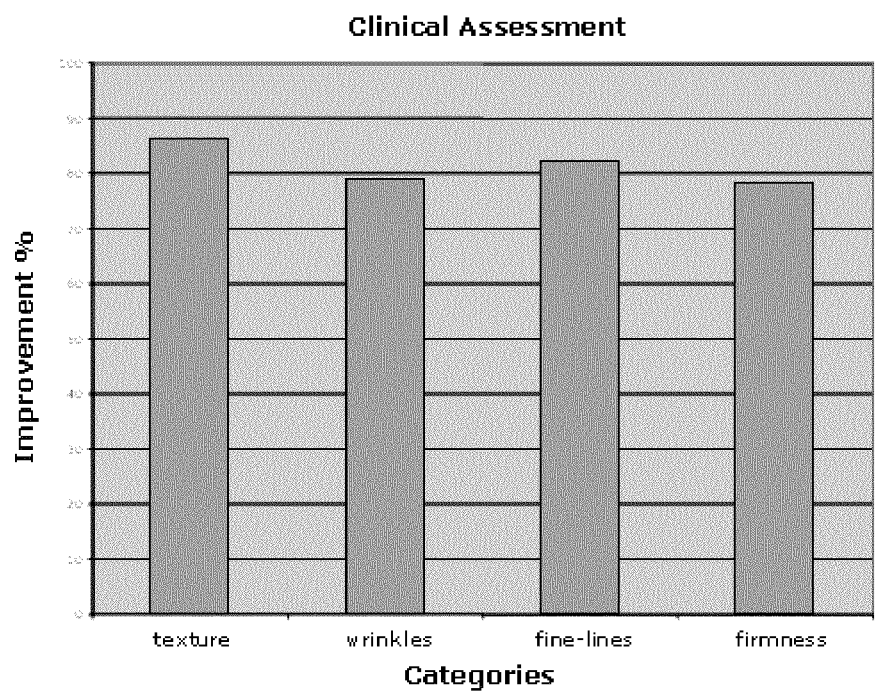
FIG. 14 shows clinical assessment (texture, wrinkles, fine-lines, firmness) as a function of percent improvement
Figure 15:
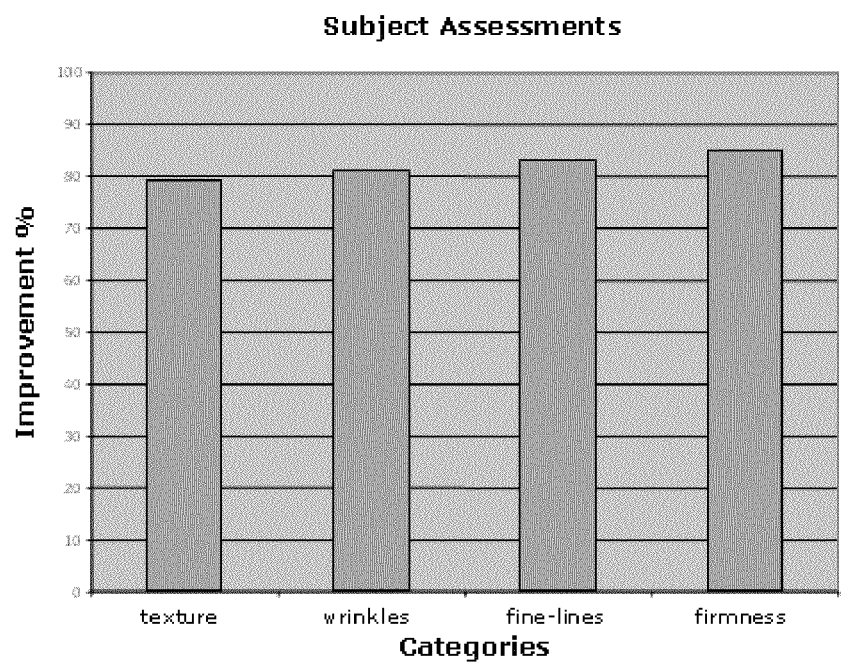
FIG. 15 shows subject assessment (texture, wrinkles, fine-lines, firmness) as a function of percent improvement.
Figure 16:
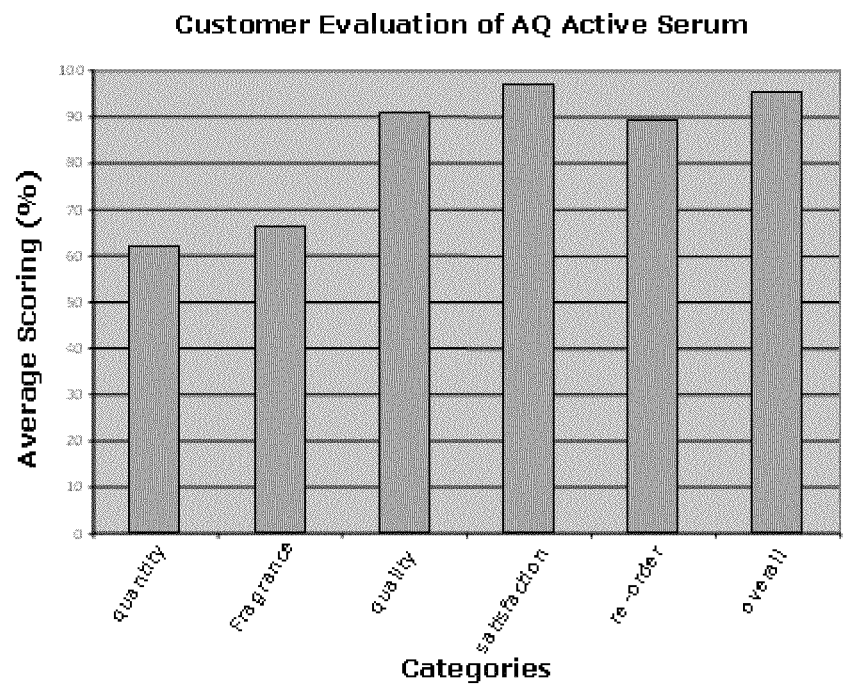
FIG. 16 shows average scoring (%) of customer evaluations (quantity, fragrance, quality, satisfaction, re-order, overall) for AQ Active Serum.
Figure 17:
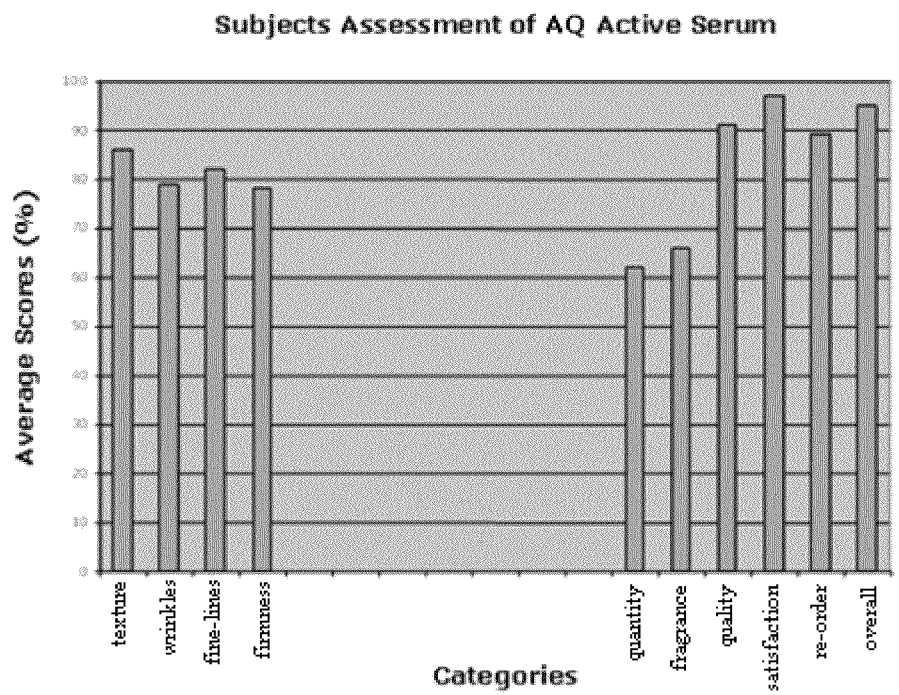
FIG. 17 shows subject assessment (%) for AQ Active Serum (texture, wrinkles, fine-lines, firmness quantity, fragrance, quality, satisfaction, re-order, overall).

All results showed a statistical significant of p=0.05. All subjects (100%) reported to have tolerated the skin serum well. All subjects (100%) liked the way the skin serum felt, while 98% would continue its regular use after the six weeks study period. Improvement is shown as difference between the averaged score before (baseline) and the averaged score after treatment expressed in percentages of the averaged baseline score and includes all 79 subjects completing the study (FIGS. 14 and 15). In conjunction with this study, we performed a comparison study, comparing AQ Active Serum to other products of similar properties or claim similar properties. This study served two purposes; 1) to show how effective AQ Active Serum compared to other products in the market, and 2) be used as a negative control for the study in addition to using a placebo (FIG. 16). In addition, subjects were asked to evaluate the AQ Active Serum in terms of quantity per bottle, quality of serum, fragrance, re-order and overall satisfaction (FIG. 17).

The before and after pictures included in this study were selected based on the following criteria:

1—Skin type and skin damage
2—Age and sex
3—Degrees of improvements

Conclusions

The study demonstrated that a skin serum (AQ Active Serum) containing a proprietary mixture of human growth factors and cytokines combined with antioxidant factors is safe and efficacious for facial skin rejuvenation in cases of mild to moderate skin damage/aging. The serum's efficacy, excellent tolerability, including the delicate periorbital skin area, and ease of use and pleasant sensory properties of the product explain why a large majority (98%) would continue regular use of AQ Active Serum.

Example 5

Vaginal Rejuvenation

The skin cream composition (AQ Vaginal Rejuvenation Serum) was formulated as above. The composition will be topically administered to the affected area of human subjects and a physical evaluation will be performed by a staff RN or staff physician.

Subjects

The study will be conducted using 20 female subjects between the ages of 25-72 yrs old. Volunteers will sign a comprehensive informed consent documents.

Subjects are given AQ Vaginal Rejuvenation Serum via administration with a single unit tube-applicator.

Example 6

AQ Lash

The skin cream composition (AQ Lash) was formulated as above. The composition (about 1 drop) was topically administered to the eyelid skin at the base of the upper and lower eyelashes in a single stroke. This was repeated 2-3 times, starting from the inner corner to the outer corner of the subject's eye. A physical evaluation was performed by a staff RN or staff physician. The treatment was carried out for 6 weeks.

Subjects

The study was conducted using 10 subjects (5 female 5 male) between the ages of 25-72 yrs old. Volunteers signed a comprehensive informed consent documents.

Figure 18:
FIG. 18 shows the results of treatment with AQ Lash. (A) before and (B) after AQ Lash application (treatment was carried out for 6 weeks).

Subjects are given AQ Lash via administration with a disposable spongiform applicator. The results are shown in FIG. 18. The AQ Lash may also be applied to eyebrows according to the desired eyebrow shape.

While a number of preferred embodiments of the invention and variations thereof have been described in detail, other modifications and methods of using and applications for the same will be apparent to those of skill in the art. Accordingly, it should be understood that various applications, modifications, materials, and substitutions may be made of equivalents without departing from the spirit of the invention or the scope of the claims. It should be understood that the invention is not limited to the embodiments set forth herein for purposes of exemplification, but is to be defined only by a fair reading of the appended claims, including the full range of equivalency to which each element thereof is entitled.

I claim:

1. A skin cream for treating a skin defect, comprising exosome enriched conditioned medium from cultured substantially homogenous foreskin derived fibroblast cells, wherein said exosomes are isolated from cultures of cells grown under conditions to promote secretion of at least one growth factor into nutrient medium, wherein:

(i) the exosomes are isolated from conditioned media that is the same as the exosome enriched conditioned medium, which fibroblast cells are from a cell line designated as ATCC Accession No. PTA-11680 or are from a cell line designated as ATCC Accession No. PTA-11681; or (ii) the exosome enriched conditioned medium is generated from transformed cells and the exosomes are isolated from conditioned medium generated from non-transformed cells; or (iii) the exosome enriched conditioned medium is generated from non-transformed cells and the exosomes are isolated from conditioned medium generated from transformed cells, and wherein said transformed cells are from the cell line designated as ATCC Accession No. PTA-11680 and said non-transformed cells are from the cell line designated as ATCC Accession No. PTA-11681.

2. The skin cream of claim 1, further comprising glycerin, *Simmondsia Chinensis* seed oil, xantham gum, hydroxyethyl acrylate/sodium acryloyldimethyl taurate copolymer, squalane, polysorbate 60, *Rosemarinus Officinalis* leaf oil, lactic acid, and chlorphenesin.

3. The skin cream of claim 2, further comprising glycerin, panthenol, biotinoyl tripeptide-1, *Lonicera Caprifolium* flower extract, *Lonicera Japonica* flower extract, 1,2-hexanediol, and caprylyl glycol.

4. The skin cream of claim 1, wherein the exosomes are isolated from conditioned media that is the same as the exosome enriched conditioned medium, which fibroblast cells are from the cell line designated as ATCC Accession No. PTA-11680.

5. The skin cream of claim 1, wherein the exosome are isolated from conditioned media that is different from the exosome enriched conditioned media.

6. The skin cream of claim 1, wherein the skin cream further comprises one or more solvents, a base solvent, one or more botanicals, and one or more emollients.

7. The skin cream of claim 1, wherein the exosomes comprise at least one molecule selected from the group consisting of a protein, DNA, RNA, and combinations thereof.

8. The skin cream of claim 7, wherein the skin cream comprises TGF Beta-1, TGF Beta-2, TGF Beta-3, IL-3, IL-6, IL-7, and IL-8, and wherein said conditioned media is present at a concentration of at least about 5-20% (wt %).

9. The skin cream of claim 8, wherein the skin cream comprises about 1-3 ng/mL TGF Beta-1, about 100-160 pg/mL TGF Beta-2, about 50-100 pg/mL TGF Beta-3, about 60 pg/mL IL-3, about 11 pg/mL IL6, about 50 pg/ML IL-7, and about 4-10 pg/mL IL-8, and
wherein said conditioned media is present at about 30-42% (wt %).

10. The skin cream of claim 1, further comprising an additional agent.

11. The skin cream of claim 10, wherein said additional agent comprises Pal-KTTKS (SEQ ID NO:2) or argireline.

12. A kit comprising: a) the skin cream of claim 1; b) a container; c) a label; d) an optional applicator; and e) instructions which provide methods of applying the skin cream.

13. The kit of claim 12, further comprising one or more ingredients selected from the group consisting of Pal-KTTKS (SEQ ID NO:2), argireline, glycerin, panthenol, biotinoyl tripeptide-1, *Lonicera Caprifolium* flower extract, *Lonicera Japonica* flower extract, 1,2-hexanediol, caprylyl glycol, *Simmondsia Chinensis* seed oil, xantham gum, hydroxyethyl acrylate/sodium acryloyldimethyl taurate copolymer, squalane, polysorbate 60, *Rosemarinus Officinalis* leaf oil, lactic acid, and chlorphenesin.

14. A composition comprising:
a) a conditioned medium or extract or concentrate thereof, from cultured substantially homogenous transformed foreskin derived fibroblast cells from a cell line designated as ATCC Accession No. PTA-11680, wherein said cells are transformed with SV40 Large T Antigen, and wherein said conditioned medium is generated by incubating a nutrient medium with said cells in two-dimensional culture under conditions adapted to promote secretion of at least one growth factor into the nutrient medium, and
b) glycerin, *Simmondsia Chinensis* seed oil, xantham gum, hydroxyethyl acrylate/sodium acryloyldimethyl taurate copolymer, squalane, polysorbate 60, *Rosemarinus Officinalis* leaf oil, lactic acid, and chlorphenesin, or
c) glycerin, panthenol, biotinoyl tripeptide-1, *Lonicera Caprifolium* flower extract, *Lonicera Japonica* flower extract, 1,2-hexanediol, and caprylyl glycol.

15. The composition of claim 14, further comprising exosome enriched conditioned medium from said cell line or from separate foreskin derived fibroblast cells.

16. A method of making a skin cream comprising:
culturing a first substantially homogenous set of cells;
harvesting the medium conditioned by said first set of cells;
optionally, culturing a second substantially homogenous set of cells;
harvesting the medium conditioned by said second set of cells;
isolating exosomes from the conditioned medium of the first or second set of cells;
adding the isolated exosomes to the conditioned medium from the first or second set of cells to form a conditioned medium containing an enriched population of exosomes;
and adding the conditioned medium containing the enriched population of exosomes to a formulation comprising one or more solvents, a base solvent, one or more botanicals, and one or more emollients to form a cream, wherein one of the set of cells comprises transformed cells from a cell line designated as ATCC Accession No. PTA-11680.

17. The method of claim 16, wherein the exosomes are isolated by a method selected from the group consisting of centrifugation, immunoaffinity, chromatography, and combinations thereof.

\* \* \* \* \*